US010184209B2

(12) United States Patent
Nakamoto et al.

(10) Patent No.: US 10,184,209 B2
(45) Date of Patent: Jan. 22, 2019

(54) CLOTHING TREATMENT APPARATUS

(71) Applicants: AQUA CO., LTD, Tokyo (JP);
QINGDAO HAIER WASHING MACHINE CO., LTD., Qingdao (CN)

(72) Inventors: Shigeharu Nakamoto, Tokyo (JP);
Hazime Suzuki, Tokyo (JP); Takayuki Nagai, Tokyo (JP); Tomohiro Yamauchi, Tokyo (JP)

(73) Assignees: AQUA CO., LTD, Tokyo (JP);
QINGDAO HAIER WASHING MACHINE., LTD., Qingdao (CN)

( * ) Notice: Subject to any disclaimer, the term of this patent is extended or adjusted under 35 U.S.C. 154(b) by 0 days.

(21) Appl. No.: 15/573,315

(22) PCT Filed: May 13, 2016

(86) PCT No.: PCT/CN2016/082114
§ 371 (c)(1),
(2) Date: Nov. 10, 2017

(87) PCT Pub. No.: WO2016/180375
PCT Pub. Date: Nov. 17, 2016

(65) Prior Publication Data
US 2018/0105973 A1    Apr. 19, 2018

(30) Foreign Application Priority Data

May 13, 2015    (JP) .................................. 2015-098512

(51) Int. Cl.
*D06F 73/02*    (2006.01)
*A61L 2/20*    (2006.01)
(Continued)

(52) U.S. Cl.
CPC .............. *D06F 73/02* (2013.01); *A61L 2/202* (2013.01); *A61L 2/24* (2013.01); *A61L 9/12* (2013.01);
(Continued)

(58) Field of Classification Search
CPC ............. A61L 2/24; A61L 2/202; D06F 73/02
See application file for complete search history.

(56) References Cited

U.S. PATENT DOCUMENTS

| 5,824,274 A * | 10/1998 | Long | C02F 1/78 708/140 |
| 2006/0263276 A1* | 11/2006 | Pattee | C01B 13/10 422/186.07 |
| 2011/0268625 A1 | 11/2011 | Chen | |

FOREIGN PATENT DOCUMENTS

| CN | 202660644 U | 1/2013 |
| CN | 203295857 U | 11/2013 |

OTHER PUBLICATIONS

PCT International Search Report and Written Opinion dated Aug. 18, 2016 from corresponding Application No. PCT/CN2016/082114, 8 pages.

* cited by examiner

*Primary Examiner* — Sean E Conley
(74) *Attorney, Agent, or Firm* — Dilworth IP, LLC

(57) ABSTRACT

A clothing treatment apparatus capable of enabling an orientation of a bag body and an orientation of an ozone supply apparatus to keep a desired relationship is provided. A clothing deodorizing apparatus comprises a bag body for accommodating clothing; an ozone supply apparatus for supplying air into the bag body; an introduction pipe for guiding the air with the ozone exhausted from the ozone supply apparatus into the bag body; a cylindrical part formed on the bag body and fixed with one end part of the intro- (Continued)

duction pipe; and an inserting port part formed on the ozone supply apparatus and configured to detachably install the other end part of the introduction pipe in a specified orientation.

3 Claims, 22 Drawing Sheets

(51) Int. Cl.
*A61L 2/24* (2006.01)
*D06M 11/34* (2006.01)
*A61L 9/12* (2006.01)

(52) U.S. Cl.
CPC ........ *D06M 11/34* (2013.01); *A61L 2202/123* (2013.01); *A61L 2202/26* (2013.01); *A61L 2209/212* (2013.01)

CLOTHING TREATMENT APPARATUS

FIELD OF THE INVENTION

The present disclosure relates to a clothing treatment apparatus for implementing treatment, such as deodorization and the like, on clothing.

BACKGROUND OF THE INVENTION

In the past, it is known a clothing refreshing apparatus which includes a storage warehouse capable of hanging the clothes on a hanging rod for storage, and introduces circulating air that has absorbed peculiar smell of clothing into an ozone deodorizer by enabling high-temperature and high-humidity air to perform internal circulation in the storage warehouse, thereby deodorizing clothing (with reference to a patent literature 1).

Since the clothing refreshing apparatus includes the storage warehouse, an apparatus body is easy to become larger. Therefore, a clothing treatment apparatus, including a bag body for accommodating the clothing and an ozone supply apparatus for supplying air with ozone into the bag body and capable of implementing treatment, such as deodorization and the like, on clothing accommodated in the bag body through ozone, in the manner of easily installing at home without large installation space, is considered to be realized.

The clothing treatment apparatus can adopt such a structure that an introduction pipe is used to connect a bag body to an ozone supply apparatus and supply air with ozone to the bag body. In this case, to separate the bag body from the ozone supply apparatus when the clothing treatment apparatus is not used, the clothing treatment apparatus can adopt such a structure that the introduction pipe fixed to a bag body side can be detachably arranged on the ozone supply apparatus.

CURRENT TECHNICAL LITERATURE

Patent Literature

Patent Literature 1: Japan specifically disclosed No. 04-327900 Bulletin

SUMMARY OF THE INVENTION

Problems to be Solved by the Disclosure

The introduction pipe is arranged on the ozone supply apparatus in a predetermined orientation in such a manner that an orientation of a bag body and an orientation of the ozone supply apparatus have a predetermined relationship, e.g., a front surface of the bag body and a front surface of the ozone supply apparatus face the same direction.

Therefore, on a fixing part of the introduction pipe and the bag body, when the introduction pipe rotates toward an in-plane direction perpendicular to an installation direction on the bag body, the orientation of the bag body and the orientation of the ozone supply apparatus may not be the desired relationship if the introduction pipe has been arranged on the ozone supply apparatus, thereby possibly causing adverse effects, such as performance degradation and the like, on the clothing treatment apparatus.

The present disclosure is a technical solution completed in view of the problem. A purpose of the present disclosure is to provide a clothing treatment apparatus capable of enabling the orientation of the bag body and the orientation of the ozone supply apparatus to keep the desired relationship.

Solution for Solving the Problems

A clothing treatment apparatus in a main embodiment of the present disclosure includes: a bag body for accommodating clothes; an ozone supply apparatus for supplying air with ozone into the bag body; an introduction pipe for guiding the air with the ozone exhausted from the ozone supply apparatus into the bag body; a fixing part formed on the bag body and fixed with one end part of the introduction pipe; and an installation part formed on the ozone supply apparatus and configured to detachably install the other end part of the introduction pipe in a specified orientation. Herein, a prevention unit for preventing the introduction pipe from rotating is arranged between one end part of the introduction pipe and the fixing part along an in-plane direction perpendicular to an installation direction of the introduction pipe to the fixing part.

Through the above structure, the introduction pipe is fixed through the prevention unit in a manner that the bag body cannot detach and rotate relative to the bag body. Thus, the orientation of the bag body and the orientation of the ozone supply apparatus can keep the desired relationship.

The clothing treatment apparatus in the present embodiment can adopt such a structure that one end part of the introduction pipe is configured to be cylindrical and the fixing part is cylindrical and encircles the one end part of the introduction pipe. In this case, the prevention unit adopts a structure including a bundling belt and a protruding part, where the bundling belt is wound on the fixing part that encircles the one end part of the introduction pipe and fastens the fixing part inwards; and the protruding part is formed on the one end part of the introduction pipe and clamped on a connecting part between a head and a belt part of the bundling belt.

Through the above structure, the bundling belt can be used to effectively prevent the introduction pipe from rotating relative to the bag body.

When the above structure is adopted, the fixing part can include a belt penetrating part and a shielding part, where the belt penetrating part can be penetrated through by the belt part; and the shielding part shields the connecting part which is exposed to the fixing part instead of penetrating through the belt penetrating part.

When such a structure is adopted, the belt part penetrates through the belt penetrating part and the connecting part which is exposed instead of penetrating through the belt penetrating part is shielded by the shielding part. Therefore, the bundling belt is difficult to be seen from outside, so that the fixing part has a beautiful appearance.

The clothing treatment apparatus in the present embodiment can also adopt a structure including a base, a supporting post and a bag body retention part, where the base is used for fixing the ozone supply apparatus; the supporting post extends upwards from the base; and the bag body retention part is arranged on an upper end of the supporting post so as to retain an upper part of the bag body in such a manner that the front surface of the bag body and one surface of the ozone supply apparatus face the same direction. In this case, the introduction pipe is arranged on the ozone supply apparatus in such a manner that the front surface of the bag body and the one surface of the ozone supply apparatus face the same direction.

Through the above structure, an upper part and a lower part of the bag body are retained respectively on the bag body retention part and the ozone supply apparatus in such a manner that the front surface of the bag body and one surface of the ozone supply apparatus face the same direction. In this case, since the introduction pipe can be prevented from rotating relative to the bag body, a torsion of the bag body is difficult to be occurred even if under the condition that the orientation of the lower part of the bag body caused by rotation of the introduction pipe is changed. By preventing the torsion of the bag body in this way, air with ozone can circulate successfully in the bag body.

Effects of the Disclosure

Through the present disclosure, a clothing treatment apparatus which is capable of enabling the orientation of the bag body and the orientation of the ozone supply apparatus to keep the desired relationship can be provided.

Effects and significance of the present disclosure can be further clarified by describing embodiments shown below. However, the following embodiments are just an example of the present disclosure. The present disclosure is not limited by disclosure in the following embodiments.

DETAILED DESCRIPTION OF THE INVENTION

A clothing deodorizing apparatus in an embodiment of a clothing treatment apparatus of the present disclosure is described below with reference to the drawings.

Figure 1:
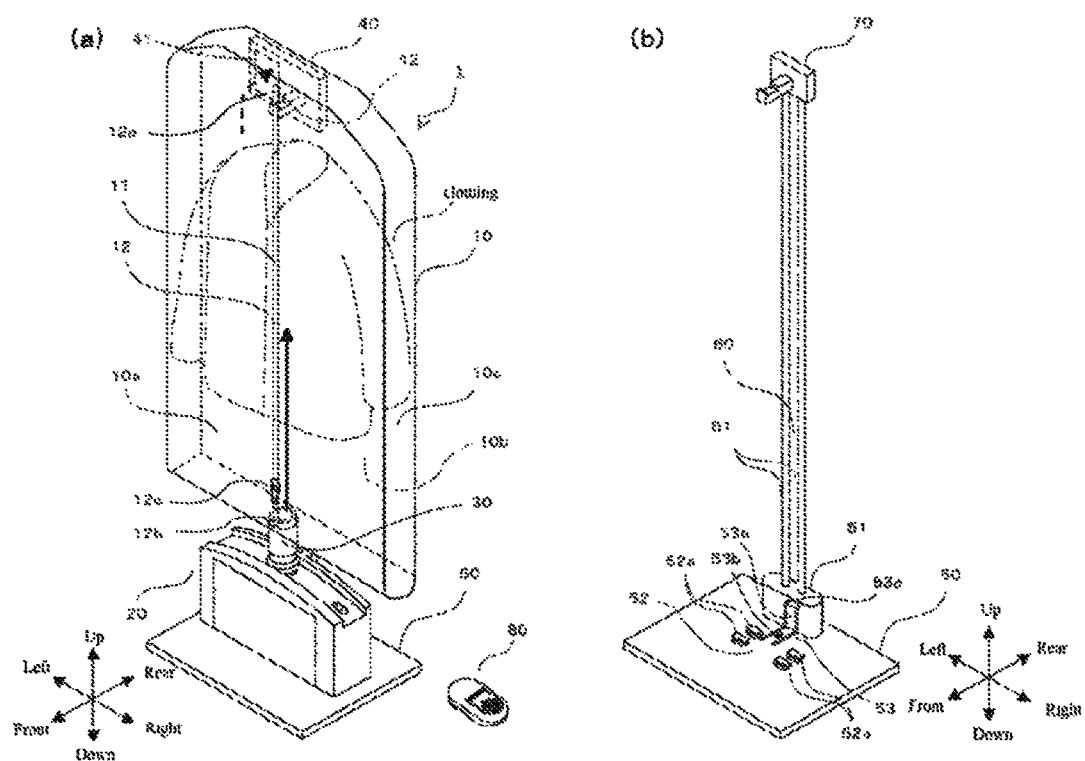
FIG. 1 is a structural diagram illustrating a clothing deodorizing apparatus according to the embodiments.

FIG. 1 is a structural diagram illustrating a clothing deodorizing apparatus 1. FIG. 1(*a*) is a perspective view illustrating the clothing deodorizing apparatus 1. FIG. 1(*b*) is a perspective view illustrating a base 50, a supporting post 60 and a bag body retention part 70 that form the clothing deodorizing apparatus 1.

By referring to FIG. 1, the clothing deodorizing apparatus 1 includes: a bag body 10, an ozone supply apparatus 20, an induction pope 30, an exhaust and clothing rack retention unit 40, a base 50, a supporting post 60, a bag body retention part 70 and a fragrance supply unit 80.

The bag body 10 accommodates various clothing such as western-style clothes, coats and the like. The bag body 10 is formed in the manner of overlapping a plurality of fabrics having the air impermeability so that tightness is adequate. The bag body 10 has an approximately lengthwise rectangular shape with flat front and rear, and is made of a front fabric 10*a* forming a front surface, a rear fabric 10*b* forming a rear surface and side fabrics 10*c* forming an upper, a lower, a left and a right side surfaces.

An up-down size of the bag body 10 is set as a size capable of accommodating the long clothing such as long shirts, long coats and the like. In addition, a front-rear size of the bag body 10 is set as a size capable of accommodating one piece of clothing. It should be noted that the up-down size of the bag body 10 can also be set as a size incapable of accommodating long clothing, and the front-rear size can also be set as a size capable of accommodating about two or three pieces of clothing arranged in order of the front and rear.

In the front surface of the bag body 10, in an approximate center of a left-right direction, a gap that forms a throwing inlet of the clothing is formed from an upper end to a lower end. A zipper 12 is arranged at the throwing inlet 11. A starting end part 12*a* and an end part 12*b* when the zipper 12 performs locking are respectively located on an upper end and a lower end of the bag body 10. A zipper slider 12*c* of the zipper 12 moves between the starting end part 12*a* and the end part 12*b*. When the zipper slider 12*c* is pulled downwards from the starting end part 12*a*, the zipper 12 is closed so that the throwing inlet 11 is locked; and when the zipper slider 12*c* is pulled upwards from the end part 12*b*, the zipper 12 is opened so that the throwing inlet 11 is opened. In this way, since a pull-down direction of the zipper slider 12*c* is set as a locking direction of the throwing inlet 11, in a locking state of the throwing inlet 11, self-weight of the zipper slider 12*c* acts in the locking direction. Therefore, it is different from a case that a pull-up direction of the zipper slider 12c forms the locking direction of the throwing inlet 11, a hidden danger that the end part 12b, i.e., a closed part of the zipper 12, is opened due to the self-weight of the zipper slider 12c does not exist.

The ozone supply apparatus 20 performs a deodorization operation for deodorizing the clothing and a fragrance increasing operation for increasing fragrance on the clothing. During the deodorization operation, the ozone supply apparatus 20 supplies air with the ozone to the bag body 10 by performing an action of enabling exhausted air to contain ozone. In addition, when the ozone supply apparatus 20 performs the fragrance increasing operation, the ozone supply apparatus 20 supplies air without the ozone to the bag body 10 by performing an action of enabling the exhausted air without containing the ozone.

The introduction pipe 30 is connected with the bag body 10 and the ozone supply apparatus 20, such that the air exhausted from the ozone supply apparatus 20 is guided into the bag body 10. During the deodorization operation, air with the ozone passes through the introduction pipe 30; and during the fragrance increasing operation, air without the ozone passes through the introduction pipe 30.

An exhaust and clothing rack retention unit 40 is arranged on an upper part of a rear surface of the bag body 10. The exhaust and clothing rack retention unit 40 integrally forms an exhaust part 41 having an ozone removing function and a clothing rack retention part 42 for retaining a clothing rack for hanging the clothing through a resin material. The air with the ozone that is beneficial for the clothing deodorization is exhausted through the exhaust part 41 from the bag body 10 to an outer side of the bag body 10. When the air passes through the exhaust part 41, the ozone included in the air is removed.

The base 50 is a flat plate with a specified shape, such as a quadrangle. The ozone supply apparatus 20 is carried on the base 50. A supporting part 51 for supporting the supporting post 60 is formed at a rear of the base 50. Moreover, a first fixing part 52 and a second fixing part 53 for fixing the ozone supply apparatus 20 in the manner of enabling the front surface of the ozone supply apparatus 20 to face a direction of the front surface of the base 50 are formed on the base 50. The first fixing part 52 is composed of a plurality of hooked claw parts 52a. The second fixing part 53 includes: an L-shaped elastic rod 53a with one end part supported by the base 50, a bulge 53b formed near the rear slightly relative to one end part of the elastic rod 53a, and a pressing part 53c formed on the other end part of the elastic rod 53a. When the pressing part 53c is pressed downwards, the elastic rod 53a generates elastic deformation and the bulge 53b is contracted into the lower part.

The supporting post 60 is composed of two rods 61. A lower end part of the supporting post 60 is arranged on the supporting part 51, and is erect relative to the base 50. The supporting post 60 may be not composed of two rods 61, but composed of one or more than three rods. In addition, a telescopic mechanism capable of adjusting the height of the supporting post 60 can also be arranged on the supporting post 60.

A bag body retention part 70 is arranged at an upper end of the supporting post 60. The bag body retention part 70 hangs and retains the bag body 10 in such a manner that the bag body 10 cannot move in any direction of front and rear, up and down and left and right.

The fragrance supply unit 80 is used when the fragrance increasing operation is performed through the ozone supply apparatus 20. The fragrance supply unit 80 is detachably arranged on the introduction pipe 30, so that air supplied to the bag body 10 contains the fragrant ingredients.

Next, structures of the bag body 10 and the introduction pipe 30 and the exhaust and clothing rack retention unit 40 which are arranged in the bag body 10 are described in detail.

Figure 2:
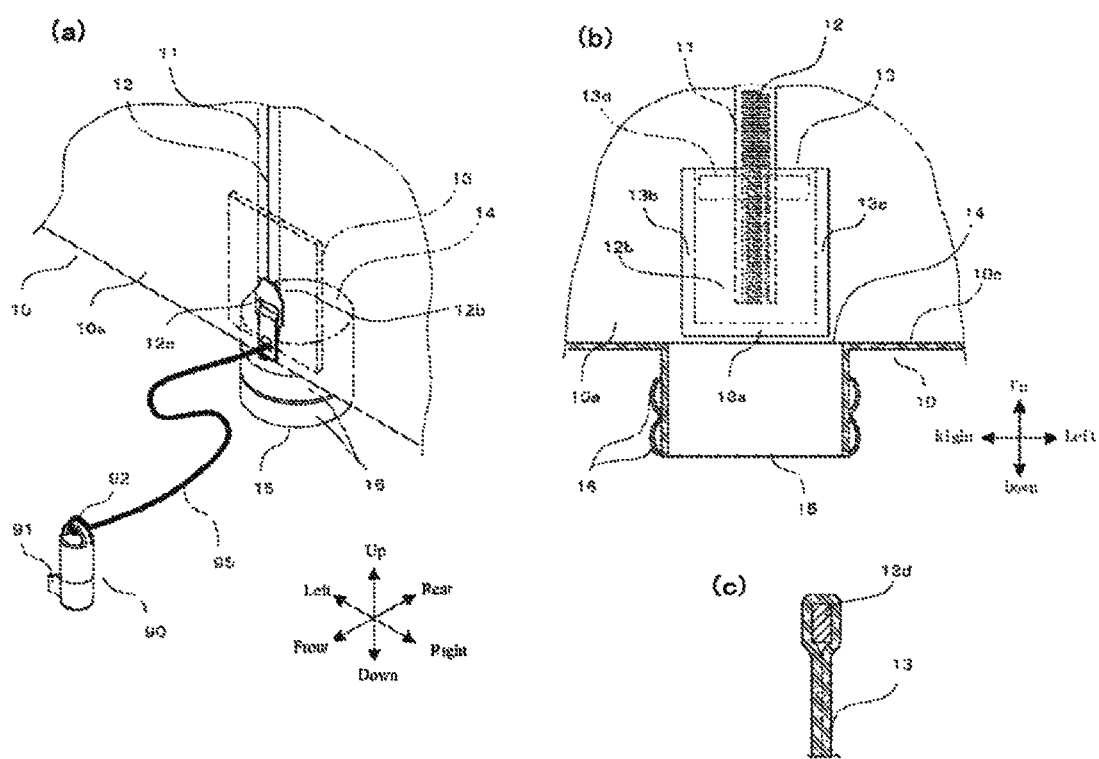
FIG. 2 is a diagram illustrating a lower central part of a bag body according to the embodiments.
Figure 3:
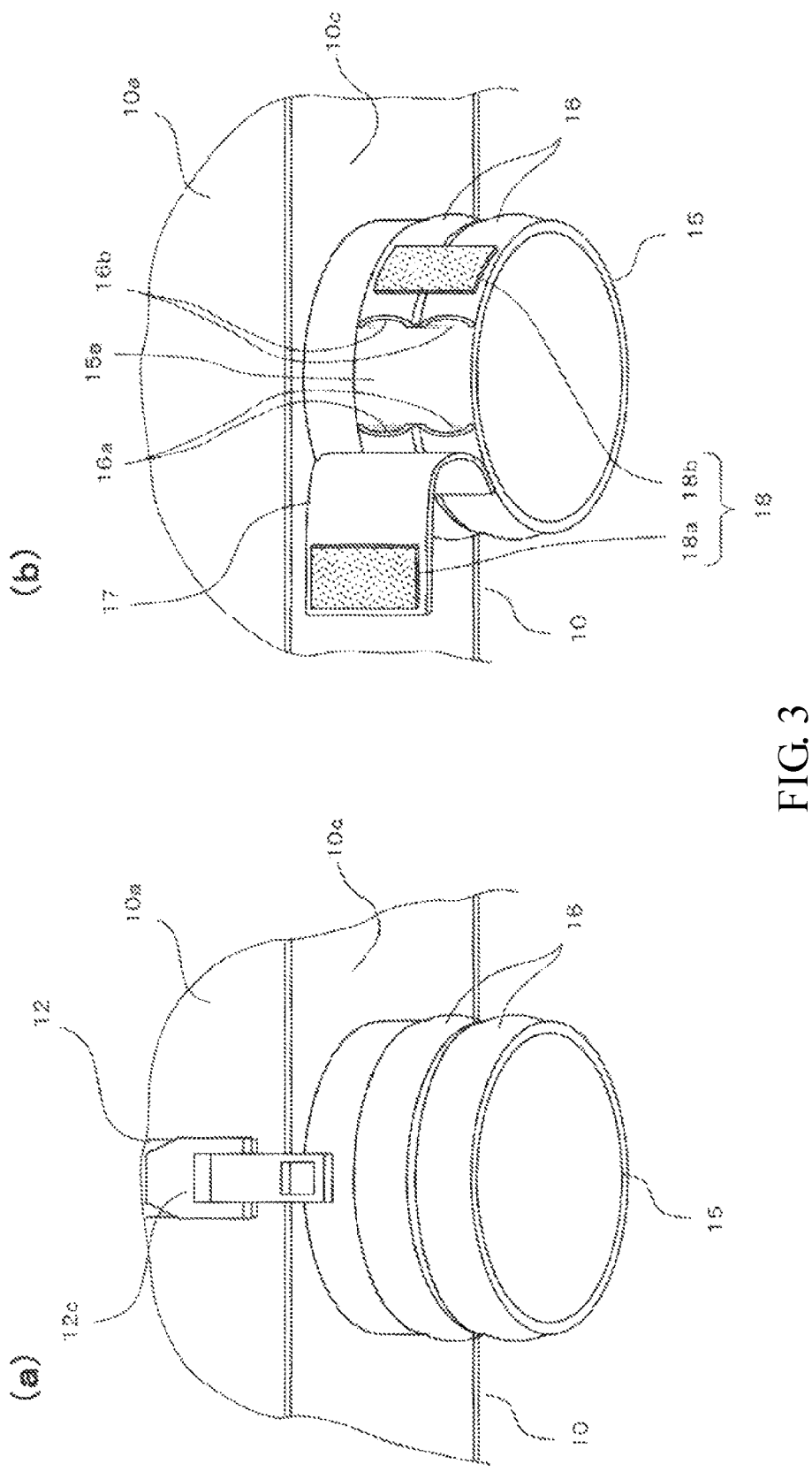
FIG. 3 is a diagram illustrating the lower central part of a bag body according to the embodiments.

FIG. 2 and FIG. 3 are diagrams illustrating a lower central part of a bag body 10. FIG. 2(a) is a front perspective view, and FIG. 2(b) is a rear section view. FIG. 3(a) is a perspective view during observation from a front lower part. FIG. 3(b) is a perspective view during observation from a rear lower part. FIG. 3(d) shows a side section of an upper part of an end hood 13.

At an inner surface of the front fabric 10a of the bag body 10, the end hood 13 is arranged in the manner of covering the end part 12b of the zipper 12, i.e., the closed part, from an inner side of the bag body 10. The end hood 13 is a rectangle shape formed by fabrics without air permeability, and a lower edge part 13a, a right edge part 13b and a left edge part 13c are tightly fixed to the inner surface of the front fabric 10a through a fixing method such as sewing, bonding and the like.

When the zipper 12 is not completely closed, the closed part of the zipper 12 is easy to become a slightly open state. As mentioned above, a periphery of the closed part is covered by the end hood. During the deodorization operation, since the air is introduced into the bag body 10, the pressure within the bag body 10 is increased; and since the pressure is increased, the end hood 13 is pushed to the front surface side of the bag body 10 and is easy to become a state close to the inner surface of the front fabric 10a. Therefore, even if the closed part of the zipper 12 is slightly opened, the air with the ozone is difficult to leak from the closed part.

It should be noted that at an upper end part of the end hood 13, filling material 13d made of polyurethane rubber and the like is accommodated in the end hood 13 in a manner that its thickness gets bigger. Thus, the zipper 12 can be prevented from being engaged to the upper end part of the end hood 13 when the zipper 12 is closed.

To detect the locking situation of the throwing inlet 11 through the zipper 12, a detection lock 90 is connected with the zipper slider 12c, and more specifically with a handle of the zipper slider 12c through a connecting rope 95. The detection lock 90 has a cylindrical shape. A protruding part 91 is formed at a lower end part of a circumferential surface of the detection lock 90, and a hanging ring part 92 for fixing the connecting rope 95 is formed at an upper end part of a circumferential surface of the detection lock 90. One end part of the connecting rope 95 is connected with the handle of the zipper slider 12c, and the other end part is connected with the hanging ring part 92. The connecting rope 95 may be a rope with a predetermined length, and for example, is realized by a silk ribbon, a chain, a metal wire and the like.

An air inlet 14 is arranged in the central part of a lower surface of the bag body 10 and a cylindrical part 15 droops from the air inlet 14. The cylindrical part 15 encircles a top end part of the introduction pipe 30 inserted into the air inlet 14. The top end part of the introduction pipe 30 is fixed to the cylindrical part 15. The cylindrical part 15 is equivalent to the fixing part of the present disclosure.

An approximately loop-shaped belt penetrating part 16 are arranged on an outer circumferential surface of the cylindrical part 15 in a vertical parallel mode along a circumferential direction. Both end parts of each belt penetrating part 16 are opened at a rear surface part 15a of the cylindrical part 15 forming the rear surface side of the bag body 10. Each belt penetrating part 16 is used for the following bundling belt to penetrate through.

A belt-shaped shielding part 17 is also arranged on an outer circumferential surface of the cylindrical part 15 in order to shield a rear surface part 15a. One end of the shielding part 17 is arranged near an open end 16a at one side of upper and lower belt penetrating parts 16. A surface of one side of a hook & loop 18, such as a hook surface 18a, is formed on the other end of the shielding part 17; and a surface of the other side of the hook & loop 18, such as a circular rough surface 18b, is formed near an open end 16b at the other side of the upper and lower belt penetrating parts 16.

Figure 4:
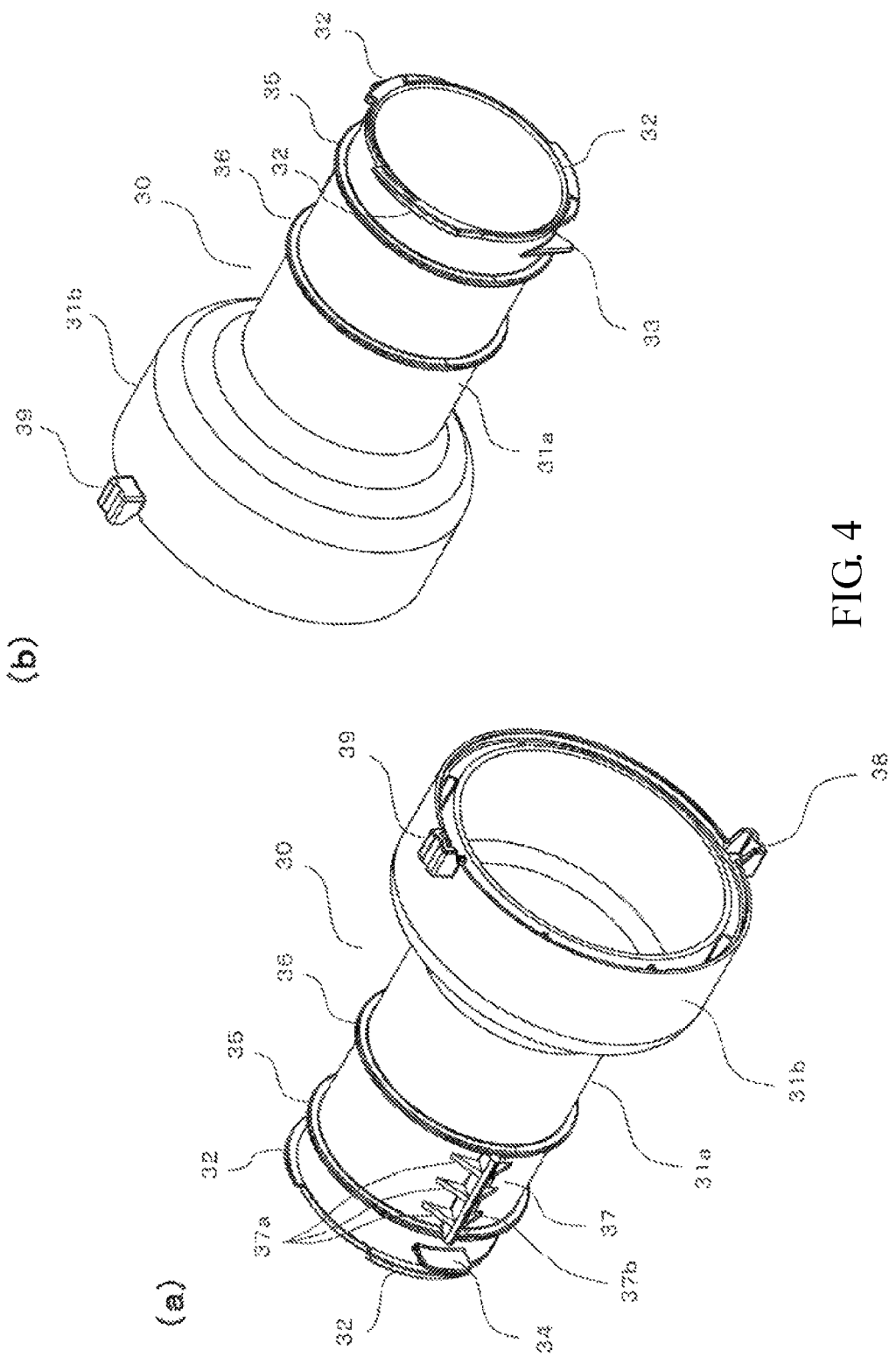
FIG. 4 is a structural diagram illustrating an introduction pipe according to the embodiments.

FIG. 4 is a structural diagram illustrating an introduction pipe 30. FIG. 4(a) is a perspective view during observation from a lower end. FIG. 4(b) is a perspective view during observation from an upper end.

The introduction pipe 30 includes a cylindrical main part 31a with a relatively small outer diameter and a cylindrical connecting part 32b with a relatively large outer diameter under the main part 31a. A boundary part between the main part 31a and the connecting part 32b has a shape that outlines are gradually centralized together.

A plurality of clamping pieces 32 for fixing the fragrance supply unit 80 are formed at an upper end of the main part 31a. In a position slightly lower than the clamping pieces 32 of the main part 31a and in positions that the introduction pipe 30 faces a front side and a rear side of the bag body 10 in a state of being arranged on the bag body 10, a front flange part 33 and a rear flange part 34 are formed. In a position slightly lower than the front flange part 33 and the rear flange part 34 of the main part 31a, an upper flange part 35 and a lower flange part 36 that have a loop-shaped are formed at a specified interval along an up-down direction. A protruding strip 37 that vertically extends is formed between the upper flange part 35 and the lower flange part 36 and in a position of facing the rear of the bag body 10 in a state of installation on the bag body 10. The protruding strip 37 is formed as an approximate triangular prism shape through triangular ribs 37a vertically parallel and longitudinal ribs 37b for connecting the triangular ribs 37a. The protruding strip part 37 is equivalent to the protruding part of the present disclosure.

A right claw part 38 and a left claw part 39 are respectively formed at a lower end of the connecting part 31b and in a positions facing a right side and a left side of the bag body 10 in a state of installation on the bag body 10.

Figure 5:
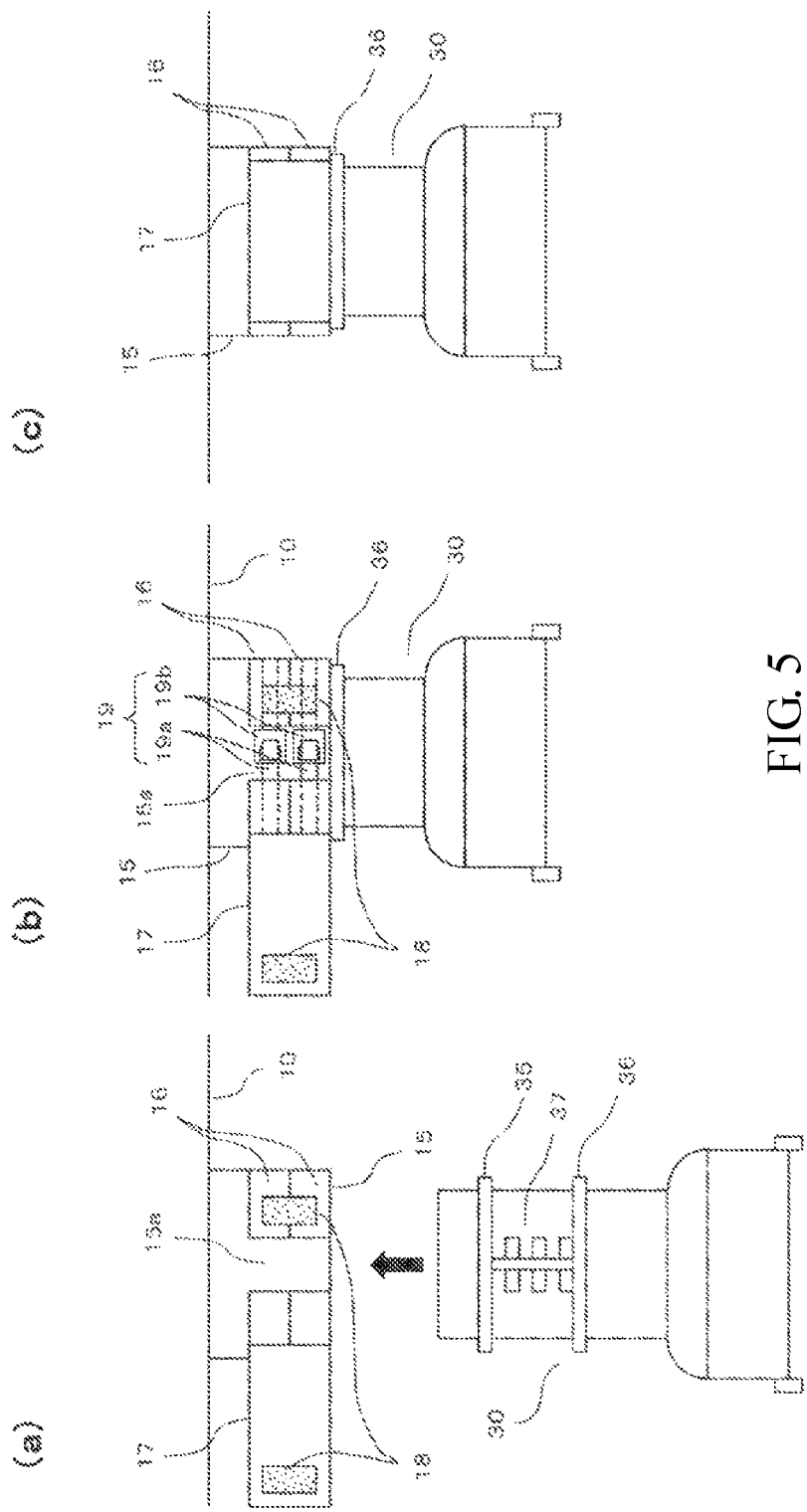
FIG. 5 is a schematic diagram illustrating a flow that the introduction pipe is arranged on a bag body according to the embodiments.

FIG. 5 is a schematic diagram illustrating a flow that the introduction pipe 30 is arranged on a bag body 10.

As shown in FIGS. 5(a) and (b), the introduction pipe 30 is inserted into a position close to the lower flange part 36 in the cylindrical part 15 in an orientation that the protruding strip part 37 is located on the rear surface part 15a. As shown in FIG. 5(b), a bundling belt 19 is inserted into a belt penetrating part 16, and wound around the cylindrical part 15. The bundling belt 19 includes a head 19a and a belt part 19b. At a rear surface part 15a, the belt part 19b penetrates through the head 19a, and the cylindrical part 15 is fastened to the inner side through the bundling belt 19. An excessive part of the belt part 19b is cut off. Then, as shown in FIG. 5(c), the other end of the shielding part 17 is fixed to the belt penetrating part 16 through a hook & loop 18. The head 19a is shielded by the shielding part 17. In this way, installation of the introduction pipe 30 on the bag body 10 is completed.

Figure 6:
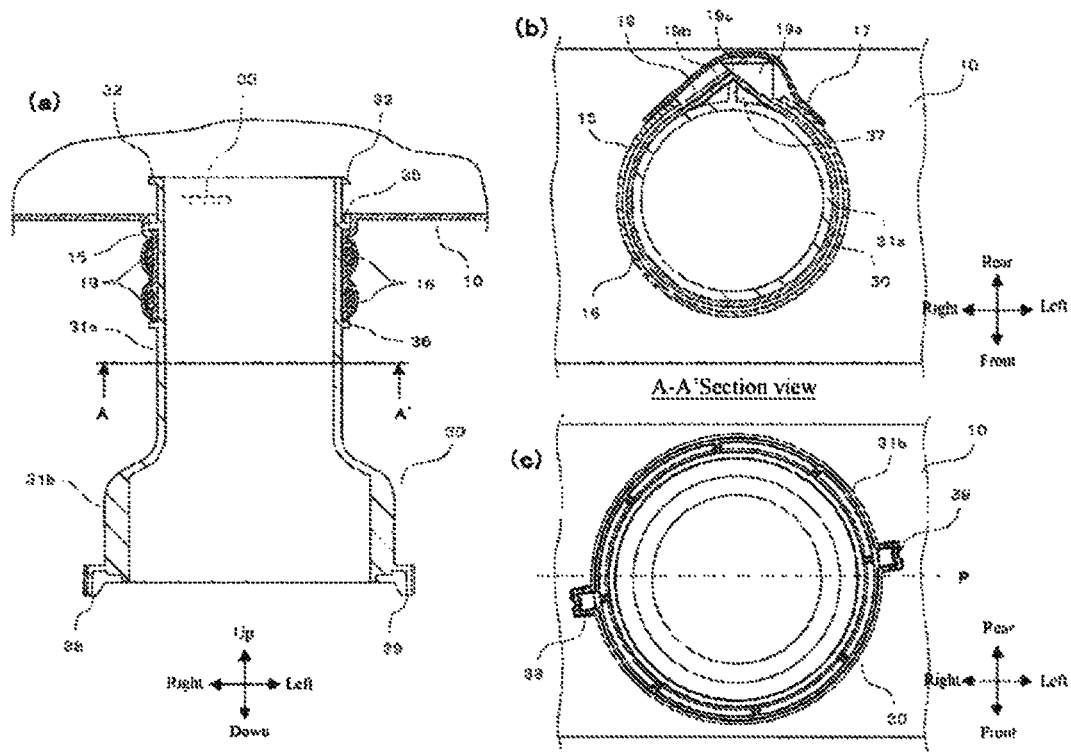
FIG. 6 is a diagram illustrating a lower central part of a bag body in a state of installing the introduction pipe according to the embodiments.

FIG. 6 is a diagram illustrating a lower central part of a bag body 10 in a state of installing the introduction pipe 30. FIG. 6(a) is a rear section view illustrating a lower central part of a bag body 10. FIG. 6(b) is an A-A' section view of FIG. 6(a). FIG. 6(c) is a diagram during observation of a lower central part of a bag body 10 from a lower side.

As shown in FIG. 6(a), in a state that the introduction pipe 30 is arranged on the cylindrical part 15 of the bag body 10, the upper and the lower flange parts 35 and 36 and the bundling belt 19 are clamped along the up-down direction, so that the introduction pipe 30 is fixed to the cylindrical part 15 along the up-down direction. Namely, the introduction pipe 30 cannot move upwards and enter the bag body 10 through the lower flange part 36, and cannot move downwards and separate from the bag body 10 through the upper flange part 35. Moreover, as shown in FIG. 6(b), a combining part 19c of the head 19a and the belt part 19b of the bundling belt 19 is clamped with the protruding strip part 37 of the introduction pipe 30 along the circumferential direction. Thus, the introduction pipe 30 is fixed to the cylindrical part 15 along the circumferential direction. In this way, the introduction pipe 30 is arranged in the manner of not separating from the bag body 10 and also not rotating relative to the bag body 10. In addition, the right claw part 38 and the left claw part 39 of the introduction pipe 30 present a predetermined position relationship relative to the bag body 10. Namely, as shown in FIG. 6(c), the right claw part 38 is in a position slightly forward than a center line P of the front-rear direction of the bag body 10, and the left claw part 39 is in a position slightly backward than the center line P of the front-rear direction of the bag body 10.

As shown in FIG. 6(a), the top part of the introduction pipe 30 is protruded in the manner of being closer to the upper part than the lower surface of the bag body 10. The front flange part 33 and the rear flange part 34 are in positions slightly close to the upper part than the lower surface of the bag body 10.

Figure 7:
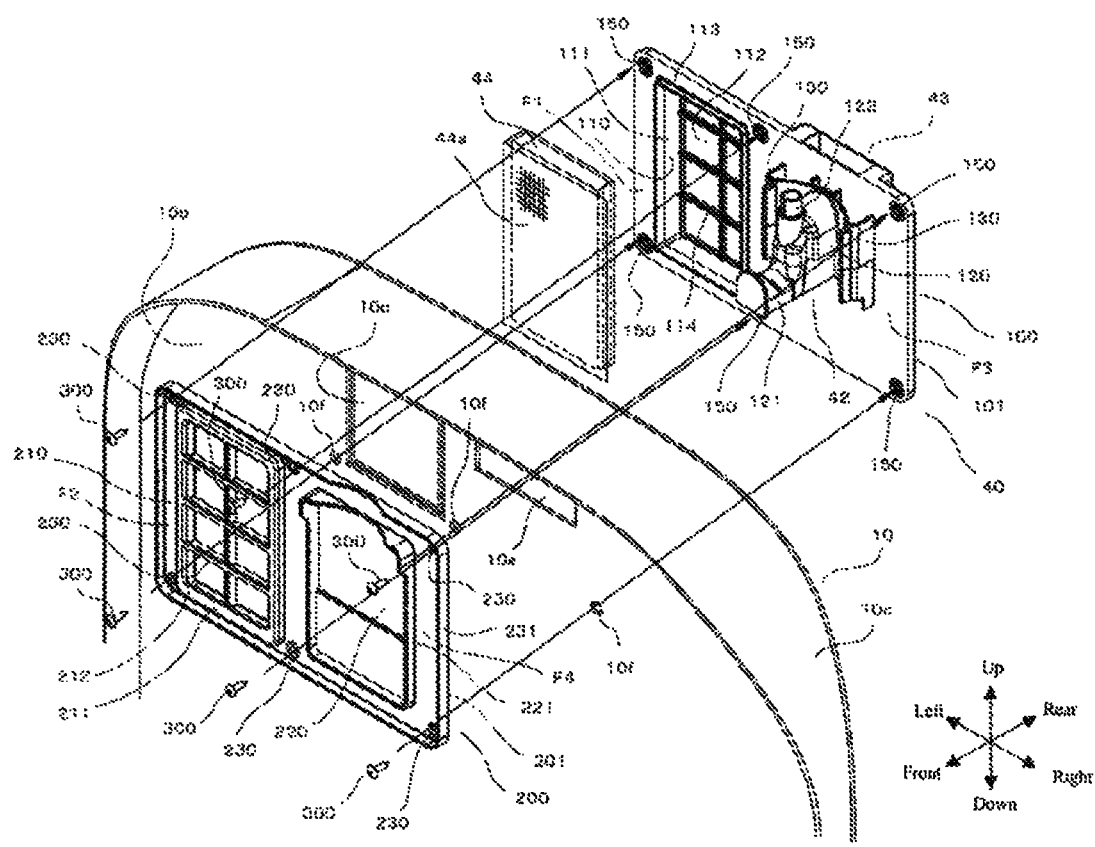
FIG. 7 is a structural diagram illustrating an exhaust and clothing rack retention unit according to the embodiments.
Figure 8:
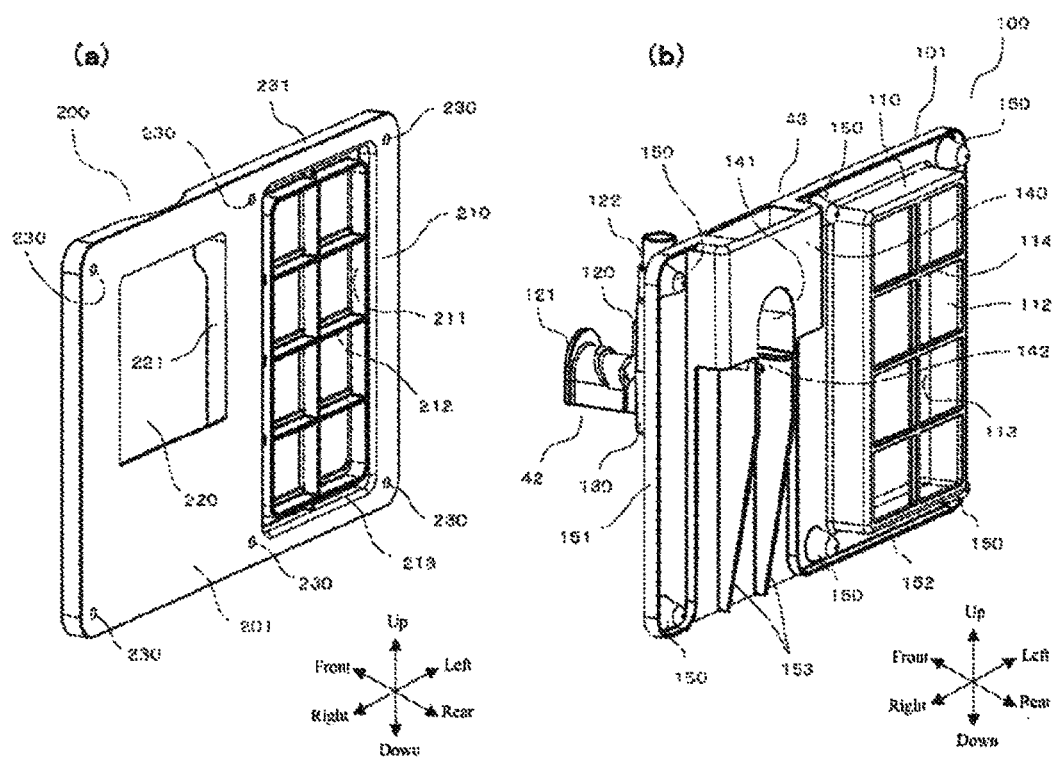
FIG. 8 is a structural diagram illustrating the exhaust and clothing rack retention unit according to the embodiments.
Figure 9:
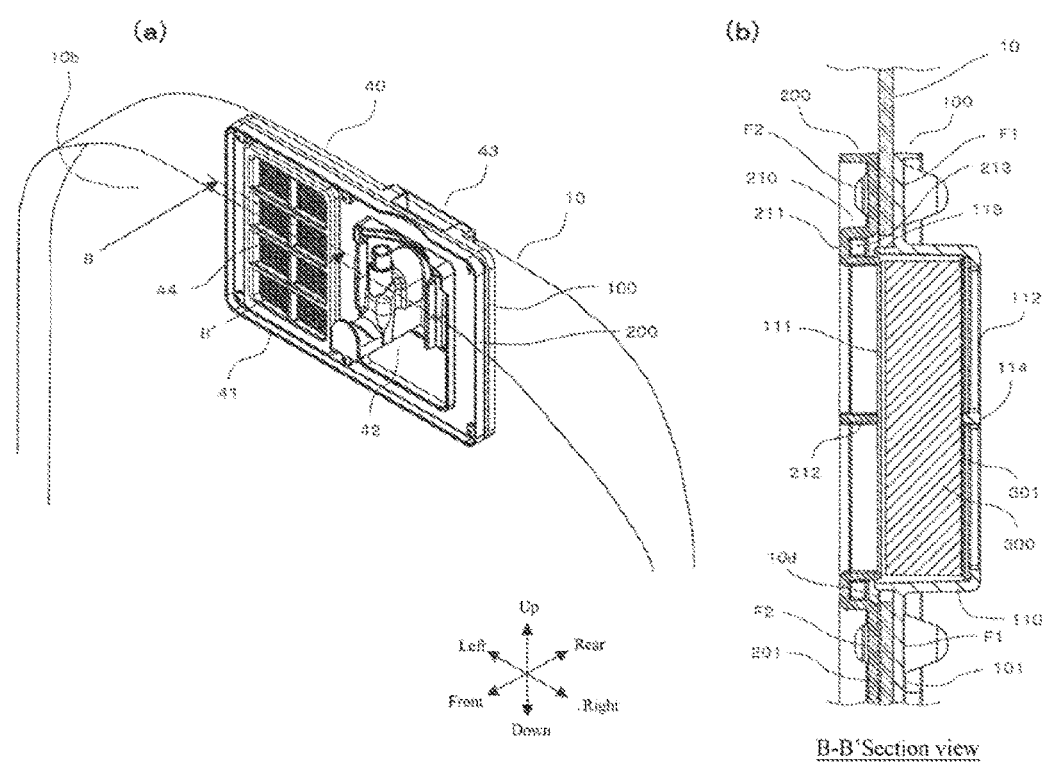
FIG. 9 is a structural diagram illustrating the exhaust and clothing rack retention unit according to the embodiments.

FIG. 7 to FIG. 10 are structural diagrams illustrating the exhaust and clothing rack retention unit 40. FIG. 7 is a perspective view illustrating an exploded exhaust and clothing rack retention unit 40 before being arranged on a bag body 10. FIGS. 8(a) and 8(b) are rear perspective views illustrating a front unit 200 and a rear unit 100 forming the exhaust and clothing rack retention unit 40 respectively. FIG. 9(a) is a perspective view illustrating the exhaust and clothing rack retention unit 40 arranged on a bag body 10. FIG. 9(b) is a B-B' section view of FIG. 9(a) that an exhaust part 41 is cut off along a horizontal direction. FIGS. 10(a) and 10(b) are a rear view and a main view illustrating an upper part of a bag body 10 respectively. It should be noted that a front surface of the bag body 10 is not shown in FIGS. 7 and 10(b) for convenience, and the bag body 10 is drawn to be transparent in FIG. 9(a).

The exhaust part 41 is formed at a left half part of the exhaust and clothing rack retention unit 40, and the clothing rack retention part 42 is formed at a front side of a right half part of the exhaust and clothing rack retention unit 40. Moreover, an installation part 43 for installing the bag body retention part 70 is formed at a rear side of the right half part of the exhaust and clothing rack retention unit 40.

The exhaust and clothing rack retention unit 40 is formed by combining the rear unit 100 and the front unit 200. The rear unit 100 and the front unit 200 are made of material, such as resin material, harder than the material of the bag body 10. The rear unit 100 and the front unit 200 respectively form constituent elements of an exhaust part 41, a clothing rack retention part 42 and an installation part 43 on a lalongate rectangular rear plate 101 and front plate 201.

The exhaust part 41 includes an exhaust pipe 110 formed on the rear plate 101 and a pipe hood 210 formed on the front plate 201. An ozone removing filter 44 is arranged within the exhaust part 41. The exhaust pipe 110 is formed in the manner of protruding backwards, and is rectangular. The front surface of the exhaust pipe 110 is opened as an inlet/outlet 111 of the ozone removing filter 44, and the rear surface is opened as an air outlet 112. The circumferential edge of the inlet/outlet 111 is enclosed by a guide frame 113 which protrudes forwards. A lattice 114 is formed at the air outlet 112. The pipe hood 210 is formed in the manner of protruding forwards slightly, and includes a rectangular outer frame 211 and a lattice 212 formed within the outer frame 211. A thickness of the outer frame 211 is greater than a thickness of the lattice 212, and a groove 213 is formed at an inner side of the outer frame 211.

The ozone removing filter 44 has a rectangular shape with flat front and rear. The ozone removing filter 44 can use, for example, an activated carbon/catalyst filter formed by transferring activated carbon and a catalyst to base material such as aluminum. A netty hood 44a covers the periphery of the ozone removing filter 44 through, thus the ozone removing filter 44 cannot be touched by hands. It should be noted that the ozone removing filter 44 can also use other filters with an ozone removing effect, such as a photocatalyst ceramic filter.

The clothing rack retention part 42 includes a first retention part 120 extending from the front surface of the rear plate 101 to the front and a second retention part 121 formed in front of the first retention part 120. A cylindrical inserting port part 122 which protrudes upwards is formed in the first retention part 120. The second retention part 121 has an upward hook shape.

Guide bodies 130 are formed on the front surface of the rear plate 101 and at a left side and a right side of the clothing rack retention part 42. In addition, an opening part 220 through which the clothing rack retention part 42 and the left and the right guide bodies 130 penetrate is formed in the front plate 201. A frame body 221 is formed around the opening part 220.

The installation part 43 includes a body part 140 and an installation hole 141. The body part 140 is formed in a square box shape, and protrudes backwards from the rear surface of the rear plate 101. The installation hole 141 is formed in the rear surface of the body part 140, and extends to the inner part of the clothing rack retention part 42 across the rear plate 101. A notch part 142 is formed on the lower surface of the installation hole 141 in the manner of facing the inner part from an opening end of the installation hole 141.

Screw holes 230 through which screws 300 penetrate are formed in the circumferential position and in positions of the upper end part and the lower end part of the center of the left-right direction of the front plate 201. Moreover, reinforcing ribs 231 which extend all over the entire circumference are formed at an outer circumferential edge of the front surface of the front plate 201.

Installation protrusions 150 for fixing the screws 300 are formed in the circumferential position and in positions of the upper end part and the lower end part of the center of the left-right direction of the rear plate 101. In addition, on the rear surface of the rear plate 101, a first reinforcing rib 151 which encircles the outer edge part of the rear plate 101 and is connected to the right lower end of the body part 140 from the right upper end of the body part 140 is formed at the right side of the installation part 43, and a second rib 152 which encircles the outer edge part of the rear plate 101 and is connected to the left lower end of the body part 140 from the left upper end of the body part 140 is formed at the left side of the installation part 43. Moreover, two third reinforcing ribs 153 which extend from both sides of the installation hole 141 to the lower side are formed on the rear surface of the rear plate 101.

On the upper part of the rear surface of the bag body 10, a first opening part 10d is formed in a position corresponding to the exhaust part 41, and a second opening part 10e is formed in a position corresponding to the clothing rack retention part 42 and the left and the right guide bodies 130. In addition, on the upper part of the rear surface of the bag body 10, insertion holes 10f are formed in positions corresponding to the screw holes 230 of the front plate 201 and the installation protrusions 150 of the rear plate 101.

When the exhaust and clothing rack retention unit 40 is assembled, firstly, the ozone removing filter 44 is accommodated in the exhaust pipe 110 of the rear unit 100. Next, the guide frame 113 is inserted into the first opening part 10d and the left and the right guide bodies 130 are inserted into the second opening part 10e, and then the rear unit 100 is arranged on the upper part of the rear surface of the bag body 10 from the outer side of the bag body 10. Next, the front unit 200 is arranged on the rear unit 100 from the inner side of the bag body 10. Then, the front unit 200 and the rear unit 100 combined by horizontally clamping the upper part of the rear surface of the bag body 10 are fixed by the screws 300. In this way, as shown in FIG. 9(a), the exhaust and clothing rack retention unit 40 is arranged on the upper part of the rear surface of the bag body 10 when being assembled.

Herein, when the rear unit 100 is arranged on the rear surface of the bag body 10, the guide frame 113 and the guide bodies 130 are respectively inserted into the first opening part 10d and the second opening part 10e for guidance. Thus, the rear unit 100 becomes easy to be arranged on the bag body 10, and the assembly of the exhaust and clothing rack retention unit 40 becomes easy.

In addition, as shown in FIG. 9(b), in the exhaust part 41, the top part of the guide frame 113 of the exhaust pipe 110 is embedded into the groove 213 of the outer frame of the pipe hood 210. Thus, since a sealing effect between the exhaust pipe 110 and the pipe hood 210 is enhanced, the air with ozone, which passes through the exhaust part 41, becomes difficult to leak from the exhaust part 41.

Then, a flat position around the exhaust pipe 110 of the rear plate 101 acts as a rear flange part F1 for covering the circumference of the first opening part 10d from the outer side, and a flat position around the pipe hood 210 of the front plate 201 acts as a front flange part F2 for covering the circumference of the first opening part 10d from the inner side. As shown in FIG. 9(b), when the exhaust part 41 is arranged on the first opening part 10d, the first opening part 10d is in a state that its circumference is sealed by the rear flange part F1 and the front flange part F2. Thus, the air with the ozone in the bag body 10 becomes difficult to leak from the first opening part 10d.

Similarly, a flat position around the clothing rack retention part 42 of the rear plate 101 and the left and the right guide bodies 130 acts as a rear flange part F3 for covering the circumference of the second opening part 10e from the outer side, and a flat position around the opening part 220 of the front plate 201 acts as a front flange part F4 for covering the circumference of the second opening part 10e from the inner side. When the clothing rack retention part 42 is arranged on the second opening part 10e, the second opening part 10e is in a state that its circumference is sealed by the rear flange part F3 and the front flange part F4. Thus, the air with the ozone in the bag body 10 becomes difficult to leak from the second opening part 10e.

Figure 10:
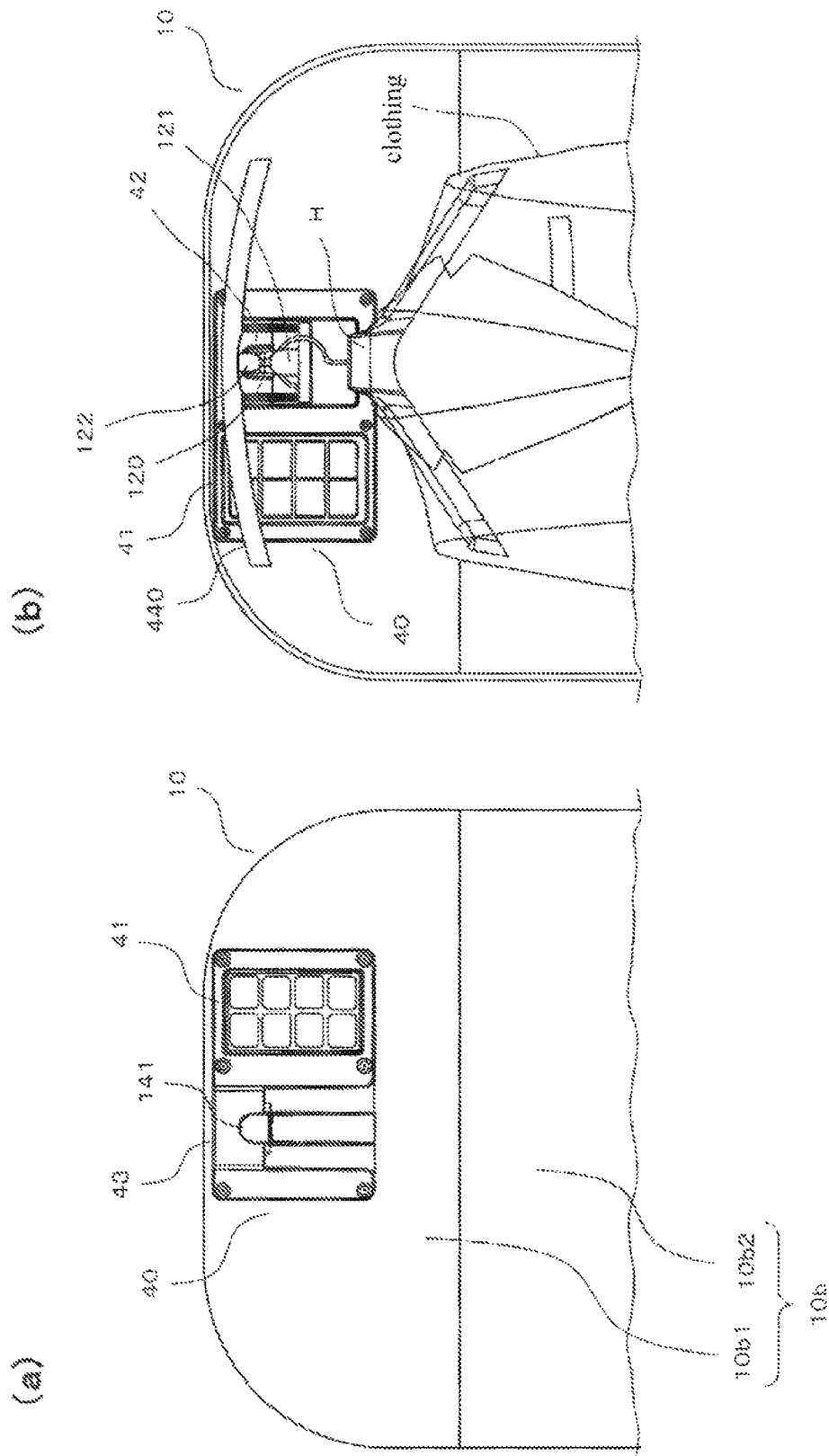
FIG. 10 is a structural diagram illustrating the exhaust and clothing rack retention unit according to the embodiments.

In a state that an exhaust and clothing rack retention unit 40 is arranged on an upper part of a rear surface of the bag body 10, as shown in FIG. 10(*a*), the installation hole 141 of the installation part 43 is located in a center of a left-right direction of the bag body 10. In addition, as shown in FIG. 10(*b*), the clothing rack retention part 42 is arranged in the bag body 10 and located in a central part of the left-right direction of the bag body 10. A hook of the clothing rack H for hanging the clothing is hooked on the second retention part 121 of the clothing rack retention part 42, and an upper hood 440 is arranged at an inserting port part 122 of the first retention part 120. The upper hood 440 is formed as a lalongate platy shape slightly bent into an arch. The upper surface of the bag body 10 is strengthened from an inner side through the upper hood 440.

The upper part 10*b*1 of the rear fabric 10*b* forming the upper part of the rear surface the bag body 10 becomes harder than other parts 10*b*2 by making a thickness become larger than a thickness of other parts 10*b*2 of the rear fabric 10*b* or changing the material of the fabric of other parts 10*b*2. Thus, the exhaust and clothing rack retention unit 40 can be reliably retained through the upper part of the rear surface of the bag body 10.

Next, the structure of the bag body retention part 70 and the installation structure of the bag body 10 about the bag body retention part 70 are described in detail.

Figure 11:
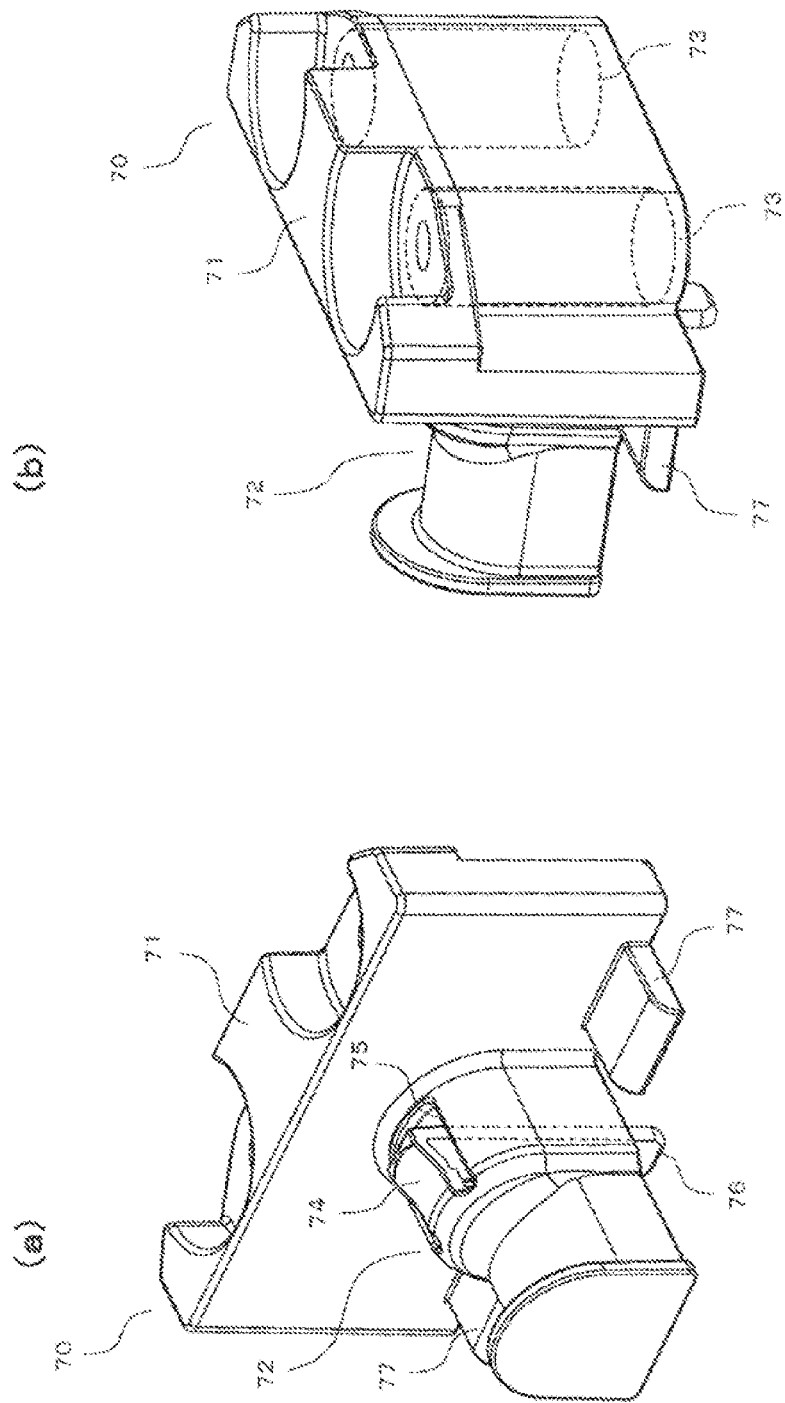
FIG. 11 is a structural diagram illustrating a bag body retention part according to the embodiments.
Figure 12:
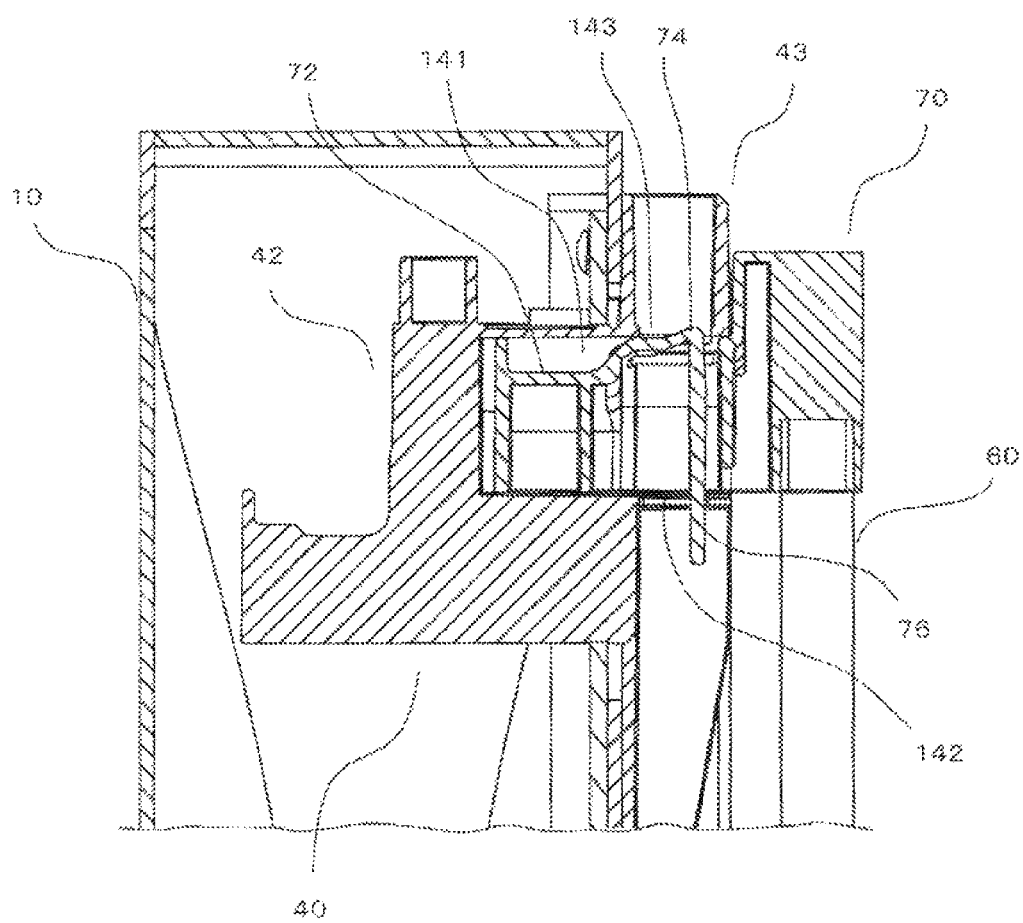
FIG. 12 is a longitudinal section view illustrating a main part in a state that the bag body is arranged on a bag body retention part according to the embodiments.

FIG. 11 is a structural diagram illustrating a bag body retention part 70. FIG. 11(*a*) is a front perspective view, and FIG. 11(*b*) is a rear perspective view. FIG. 12 is a longitudinal section view illustrating a main part in a state that the bag body 10 is arranged on a bag body retention part 70.

The bag body retention part 70 includes a box-shaped body part 71 and a retention part 72 which extends forwards from the body part 71. Cylindrical insertion holes 73 are formed at a left side and a right side of the body part 71. An upper end part of a rod 61 is inserted into the insertion holes 73.

A clamping claw part 74 is formed on an upper part of a root part of the retention part 72. An opening part 75 is formed around the clamping claw part 74. An inner part of the retention part 72 is hollow, and an operation sheet 76 which droops from the clamping claw part 74 protrudes to the lower part of the retention part 72 from the inner parts of the opening part 75 and the retention part 72. When the operation sheet 76 is pulled to the lower side, the clamping claw part 74 is contracted into the lower side.

The top part of the retention part 72 has an upward hook shape. When the bag body 10 is not arranged on the bag body retention part 70, the clothing rack can be hooked on the top part. Supporting sheets 77 are formed at a lower end of the front surface of the body part 71 and locate on the left side and the right side of the retention part 72.

As shown in FIG. 12, under the condition that the bag body 10 is arranged on the bag body retention part 70, the retention part 72 of the bag body retention part 70 is inserted into the installation hole 141 of the exhaust and clothing rack retention unit 40 by user. During insertion, the operation sheet 76 of the retention part 72 passes through the notch part 142 of the installation hole 141. A clamping hole 143 is formed in the upper part of the inlet part of the installation hole 141. When the retention part 72 is inserted into the installation hole 141 totally, the clamping claw part 74 is clamped with the clamping hole 143. Thus, the retention part 72 is not separated from the installation hole 131. The bag body 10 is fixed in the manner of not moving towards the up-down direction and the left-right direction and not separating forwards relative to the bag body retention part 70. In addition, the lower surface of the installation part 43, although not shown in FIG. 12, is supported by the left and right supporting sheets 77. As shown in FIG. 1(*a*), in a state of being fixed to the bag body retention part 70, the front surface of the bag body 10 faces the front direction of the base 50.

The operation sheet 76 is pulled to the lower part by user so that the clamping claw part 74 is contracted and the bag body 10 is moved to the front part, thereby removing the bag body 10 from the bag body retention part 70.

Next, a detailed structure of the ozone supply apparatus 20 is described.

Figure 13:
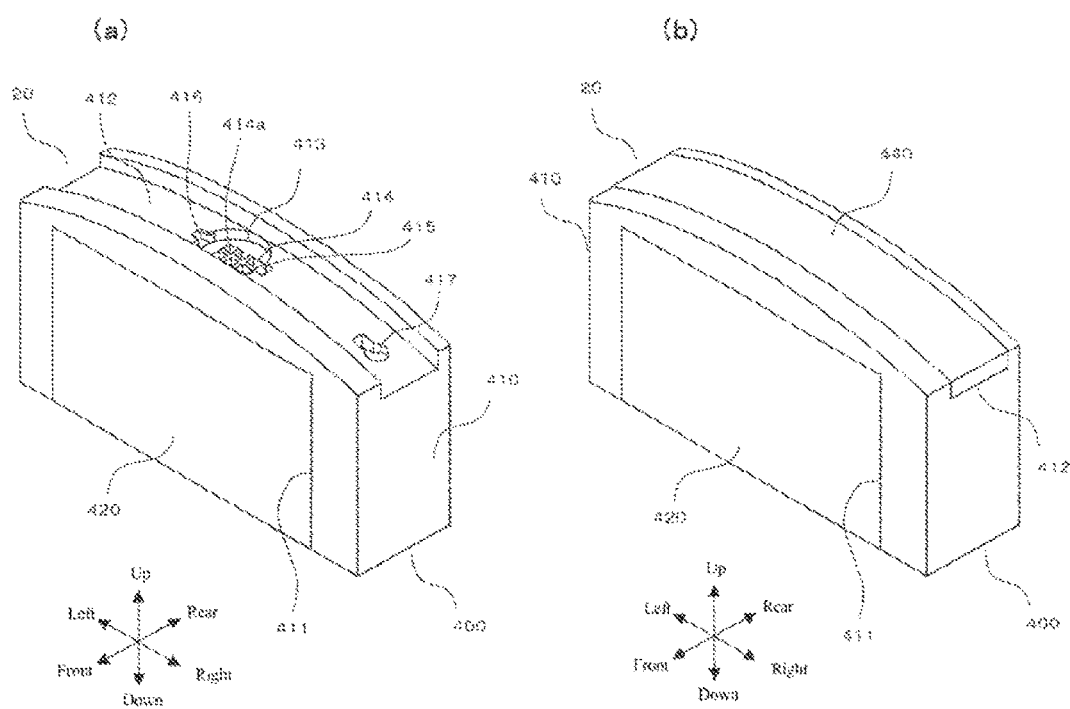
FIG. 13 is a structural diagram illustrating an ozone supply apparatus according to the embodiments.
Figure 14:
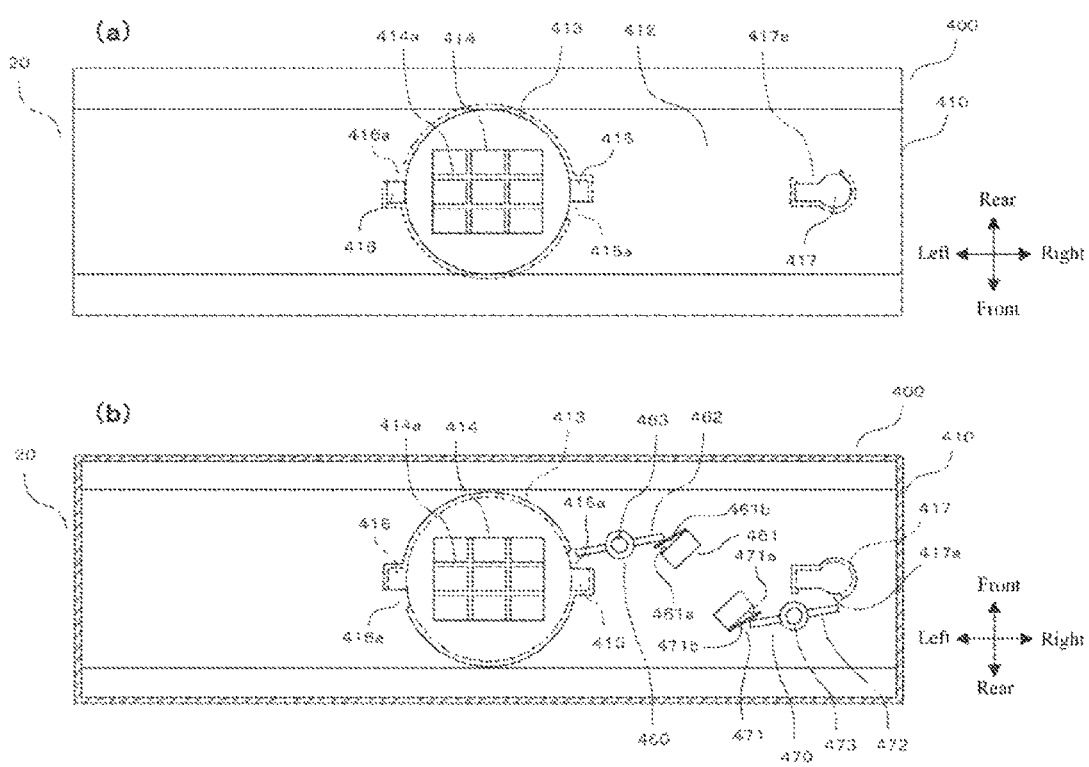
FIG. 14 is a structural diagram illustrating the ozone supply apparatus according to the embodiments.
Figure 15:
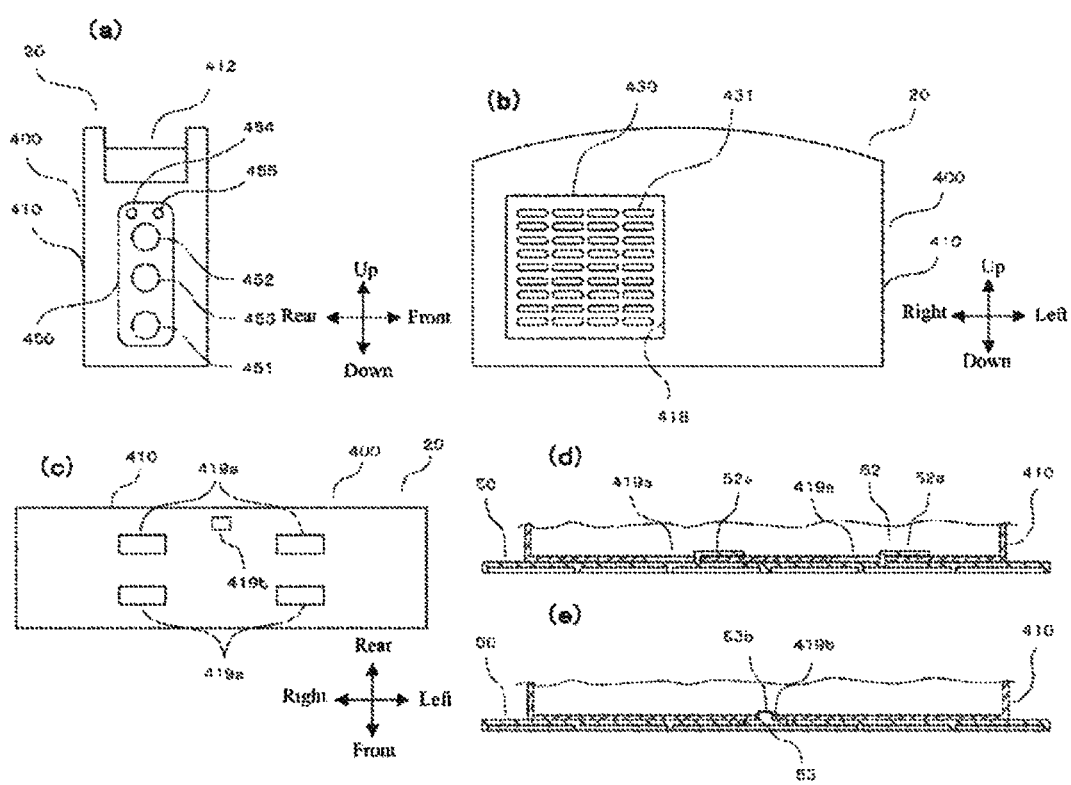
FIG. 15 is a structural diagram illustrating the ozone supply apparatus according to the embodiments.
Figure 16:
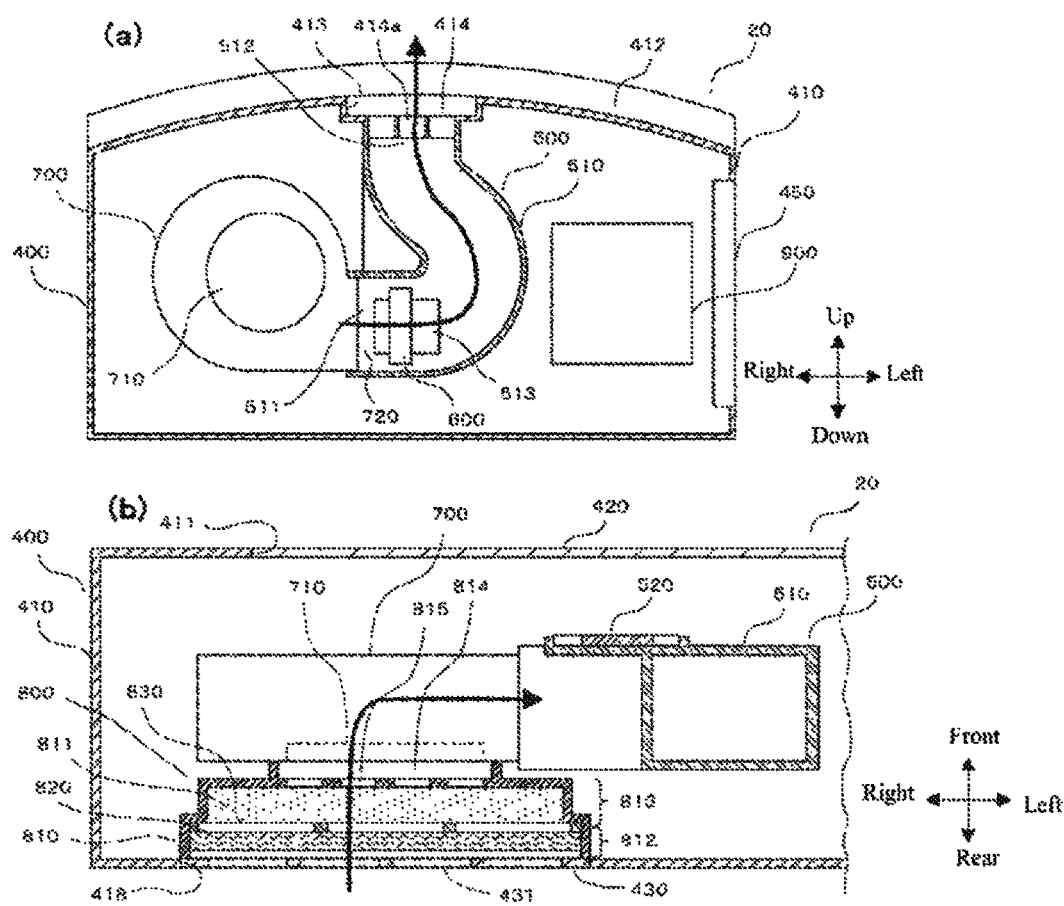
FIG. 16 is a structural diagram illustrating the ozone supply apparatus according to the embodiments.

FIG. 13 to FIG. 16 are structural diagrams illustrating an ozone supply apparatus 20. FIG. 13(*a*) is a perspective view illustrating an ozone supply apparatus 20 in a state without installing an upper hood 440. FIG. 13(*b*) is a perspective view illustrating an ozone supply apparatus 20 in a state with an upper hood 440. FIG. 14(*a*) is a top view illustrating an ozone supply apparatus 20. FIG. 14(*b*) is a cross section view for observing an upper surface of a housing 400 of an ozone supply apparatus 20 from an inner side. FIGS. 15(*a*) to (*c*) are a left view, a rear view and a bottom view illustrating an ozone supply apparatus 20 respectively. FIGS. 15(*d*) and (*e*) are side section views illustrating a main part of an ozone supply apparatus 20 in a state of being fixed to the base 50. FIG. 16(*a*) is a longitudinal section view for observing an ozone supply apparatus 20 from a rear. FIG. 16(*b*) is a cross section view for overlooking a main part of an ozone supply apparatus 20. It should be noted that a right inserting concave part 415, a left inserting concave part 416, a lock inserting concave part 417, a pipe detection part 460 and a lock detection part 470 are not shown in FIG. 16(*a*).

The ozone supply apparatus 20 includes a housing 400, a vent pipe 500, an ozone generator 600, a blowing fan 700, an air suction unit 800 and a control unit 900.

The housing 400 includes: a housing body 410, a front hood 420, an air suction hood 430, an upper hood 440 and an operation part 450. As shown in FIG. 13(*a*), the housing body 410 has a lalongate rectangular shape with an upper surface gently bent. A front surface opening part 411 is formed on a front surface of the housing body 410. The front surface opening part 411 is locked detachably through the front hood 420.

A concave part 412 formed on the upper surface of the housing body 410 has the same shape as the upper hood 440. An inserting port part 413 arranged in the center of the concave part 412 has a circular shape. An exhaust port 414 with a lattice-shaped rib 414*a* for restricting the flow is formed at the inserting port part 413. The inserting port part 413 is equivalent to the installation part of the present disclosure.

A right inserting concave part 415 and a left inserting concave part 416 with shapes corresponding to the shapes of the right claw part 38 and the left claw part 39 of the introduction pipe 30 are formed on the concave part 412 and locate at the left side and the right side of the inserting port part 413. As shown in FIGS. 14(*a*) and (*b*), a right opening part 415*a* is formed at a front side of the right inserting concave part 415 in such a manner that the right claw part 38 inserted into the right inserting concave part 415 only moves toward a right turning direction by about an amount of one right claw part 38. Similarly, a left opening part 416*a* is formed at a rear side of the left inserting concave part 416 in such a manner that the left claw part 39 inserted into the left inserting concave part 416 only moves toward a right turning direction by about an amount of one left claw part 39.

The lock inserting concave part 417 with a shape corresponding to the shape of the detection lock 90 is formed at a right end part of the concave part 412. As shown in FIGS. 14(a) and 14(b), an opening part 417a is formed in a side surface of the rear side of the lock inserting concave part 417.

As shown in FIG. 13(b), when the clothing deodorizing apparatus 1 is not used, the upper hood 440 removed from the bag body 10 can be arranged on the concave part 412. Thus, since a retention place of the upper hood 440 removed from the bag body 10 is ensured, the upper hood 440 can be prevented from being lost when not used. In addition, dust can be prevented from entering the housing 400 from the exhaust port 414 and the lock inserting concave part 417 when the clothing deodorizing apparatus is not used.

As shown in FIG. 14(b), the pipe detection part 460 and the lock detection part 470 are arranged at an inner side of the upper surface of the housing body 410. The pipe detection part 460 includes a detection switch 461 and a relay rod 462. The detection switch 461 has a switch part 461a and a rod part 461b for pressing the switch part 461a. The relay rod 462 can be arranged freely rotatably on a rotating shaft 463 formed at the inner side of the upper surface of the housing body 410. One end of the relay rod 462 is located near the right inserting concave part 415, and the other end comes into contact with the detection switch 461. The lock detection part 470 includes a detection switch 471 and a relay rod 472. The detection switch 471 has a switch part 471a and a rod part 471b for pressing the switch part 471a. The relay rod 472 can be arranged freely rotatably on a rotating shaft 473 formed at the inner side of the upper surface of the housing body 410. One end of the relay rod 472 is located near the lock inserting concave part 417, and the other end comes into contact with the detection switch 471.

As shown in FIG. 15(a), the operation part 450 is arranged on a left side of the housing body 410. The operation part 450 includes a power button 451, a deodorization button 452 and a fragrance increasing button 453. The power button 451 is a button for switching on or off a power supply of the clothing deodorizing apparatus 1. The deodorization button 452 is a button for starting deodorization operation. The fragrance increasing button 453 is a button for starting fragrance increasing operation. In addition, the operation part 450 includes a first informing part 454 and a second informing part 455. The first informing part 454 includes, for example, LED, and an illuminated lamp is used for informing that the introduction pipe 30 is not connected with the ozone supply apparatus 20. The second informing part 455 includes, for example, LED, and an illuminated lamp is used for informing that the throwing inlet 11 of the bag body 10 is not locked.

As shown in FIG. 15(b), an air suction port 418 is formed in a rear surface of the housing body 410. The air suction port 418 is detachably locked through the air suction hood 430. A plurality of air suction holes 431 are formed in the air suction hood 430.

As shown in FIG. 15(c), at a bottom surface of the housing body 410, a first installation hole 419a is formed in a position corresponding to each claw part 52a of the first fixing part 52 of the base 50, and a second installation hole 419b is formed in a position corresponding to the bulge 53b of the second fixing part 53. After a user presses the pressing part 53c of the second fixing part 53 downwards to contract the bulge 53b, when the claw part 52a loads the ozone supply apparatus 20 on the base 50 through the first installation hole 419a so as to transversely slide the ozone supply apparatus 20, as shown in FIG. 15(d), the claw part 52a is clamped with a bottom surface of the housing body 410. Then, when the user stops pressing the pressing part 53c, as shown in FIG. 15(e), the bulge 53b is embedded into the second installation hole 419b. Thus, the ozone supply apparatus 20 is fixed to the base 50 in the manner of not moving in directions of up and down, front and rear and left and right. Therefore, the ozone supply apparatus 20 can be prevented from falling due to a force applied to the ozone supply apparatus 20 when the bag body 10 is inflated because of the air supplied by the ozone supply apparatus 20.

A vent pipe 500, an ozone generator 600, a blowing fan 700, an air suction unit 800 and a control unit 900 are configured within the housing 400.

As shown in FIGS. 16(a) and (b), the vent pipe 500 includes a pipe body 510 and a pipe cover 520. An induction port 511 of the pipe body 510 is connected with the exhaust port 720 of the blowing fan 700, and an eduction port 512 is connected with the exhaust port 414. The ozone generator 600 is arranged near the induction port 511 in the pipe body 510. The pipe body 510 has the following shape: the pipe body 510 extends upwards to the eduction port 512 after bending in the manner of extending from the induction port 511 to the left and beginning to go back to the right over a part of the configuration position of the ozone generator 600. Namely, a part of a downstream side of the pipe body 510 forming the ozone generator 600 crawls in an S shape.

The ozone generator 600 is a discharge type ozone generator. Discharge such as corona discharge, silent discharge and the like is generated between a pair of electrodes, and ozone is generated through the air between a pair of electrodes. At a front surface of the pipe body 510, an opening part 513 is formed in a position corresponding to the ozone generator 600. The opening part 513 is locked through the pipe cover 520. The user can remove the front hood 420 and the pipe cover 520, so as to clean the electrodes through the opening part 513 to maintain the ozone generator 600.

The blowing fan 700 is a centrifugal fan, a suction inlet 710 is arranged in its side surface, and an exhaust port 720 is arranged in its circumferential surface. The suction inlet 710 is opposite to the air suction port 418 on the rear surface of the housing 400. The blowing fan 700 obtains the air from the suction inlet 710, and delivers the obtained air to the ozone generator 600 in the vent pipe 500. The blowing fan 700 can also be other fans besides the centrifugal fan, such as an axial flow fan.

As shown in FIG. 16(b), an air suction unit 800 is arranged between the air suction port 418 of the housing 400 and the suction inlet 710 of the blowing fan 700. The air suction unit 800 includes an air suction pipe 810, a dust filter 820 and an ozone removing filter 830.

The air suction pipe 810 is divided into a first filter accommodating part 812 at a side of the air suction port 418 and a second filter accommodating part 813 at a side of the blowing fan 700 through a latticed dividing plate 811. A dust filter 820 is accommodated in the first filter accommodating part 812, and an ozone removing filter 830 is accommodated in the second filter accommodating part 813. The dust filter 820 removes dust included in the air obtained from the air suction port 418. The ozone removing filter 830 removes the ozone included in the air passing through the dust filter 820. The ozone removing filter 830, which is identical with the ozone removing filter 44 of the exhaust and clothing rack retention unit 40, can be an activated carbon/a catalyst filter.

The air suction pipe 810 is provided with a connecting part 814 connected with the suction inlet 710 of the blowing fan 700. The connecting part 814 is connected to the second filter accommodating part 813 through a communication hole 815.

The control unit 900 includes a CPU, a memory and the like to control the ozone generator 600 and the blowing fan 700.

Figure 17:
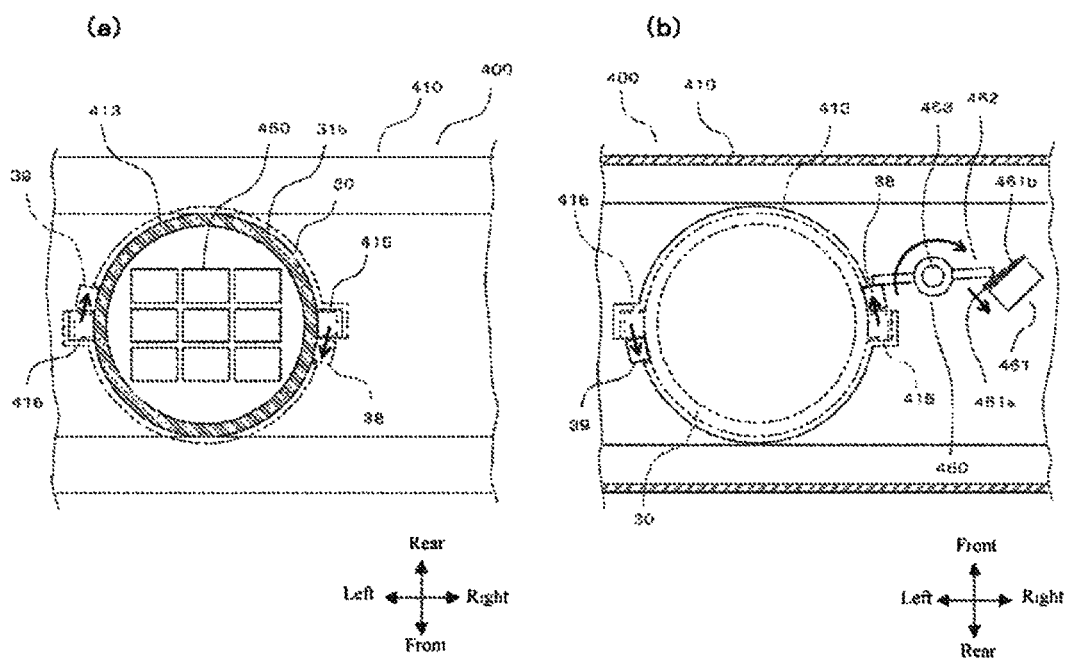
FIG. 17 is a diagram illustrating a connection of an introduction pipe to an ozone supply apparatus and a connection detection made through a pipe detection part according to the embodiments.

Next, with reference to FIG. 17, a connection of the introduction pipe 30 to the ozone supply apparatus 20 and a connection detection made by the pipe detection part 460 are described.

When the introduction pipe 30 is connected to the ozone supply apparatus 20, as shown in FIG. 17(*a*), the connecting part 31*b* of the introduction pipe 30 is inserted into the inserting port part 413 in the manner of respectively inserting the right claw part 38 and the left claw part 39 into the right inserting concave part 415 and the left inserting concave part 416. Then, when the introduction pipe 30 is observed from the upper part and rotates to the right, the right claw part 38 and the left claw part 39 respectively move to the inner side of the upper surface of the housing body 410 through the right opening part 415*a* and the left opening part 416*a*, and are clamped with the upper surface of the housing body 410. Thus, the introduction pipe 30 does not fall off upwards.

As described in FIG. 6(*c*), since the right claw part 38 is in a position slightly forward than a center line P of the front-rear direction of the bag body 10, and the left claw part 39 is in a position slightly backward than the center line P of the front-rear direction of the bag body 10, as shown in FIG. 1(*a*), the introduction pipe 30 is connected with the ozone supply apparatus 20 in such a manner that the front surface of the bag body 10 faces the front direction of the ozone supply apparatus 20, i.e., the front direction of the base 50. In addition, as mentioned above, the exhaust and clothing rack retention unit 40 is fixed to the bag body retention art 70 in such a manner that the front surface of the bag body 10 faces the front direction of the base 50. Therefore, the bag body 10 is hanged above the ozone supply apparatus 20 in such a state that the upper part and the lower part are hardly distorted. Thus, the clothing can be well accommodated in the bag body 10, and the air with the ozone can be successfully circulated in the bag body 10.

In this way, the introduction pipe 30 is connected with the ozone supply apparatus 20.

As shown in FIG. 17(*b*), when the right claw part 38 moves to the inner side of the upper surface of the housing body 410, one end of the relay rod 462 is pressed by the right claw part 38. The relay rod 462 rotates, a rod part 461*b* is pressed by the other end of the relay rod 462; and a switch part 461*a* is pressed by the pressed rod part 461*b*. Thus, the detection switch 461 detects that the introduction pipe 30 has been mounted on the inserting port part 413.

It should be noted that when the introduction pipe 30 is removed from the inserting port part 413, the rod part 461*b* rotates the relay rod 462 through elasticity itself, and simultaneously returns to an initial position. Thus, the detection switch 461 detects that the introduction pipe 30 has been removed from the inserting port part 413.

Figure 18:
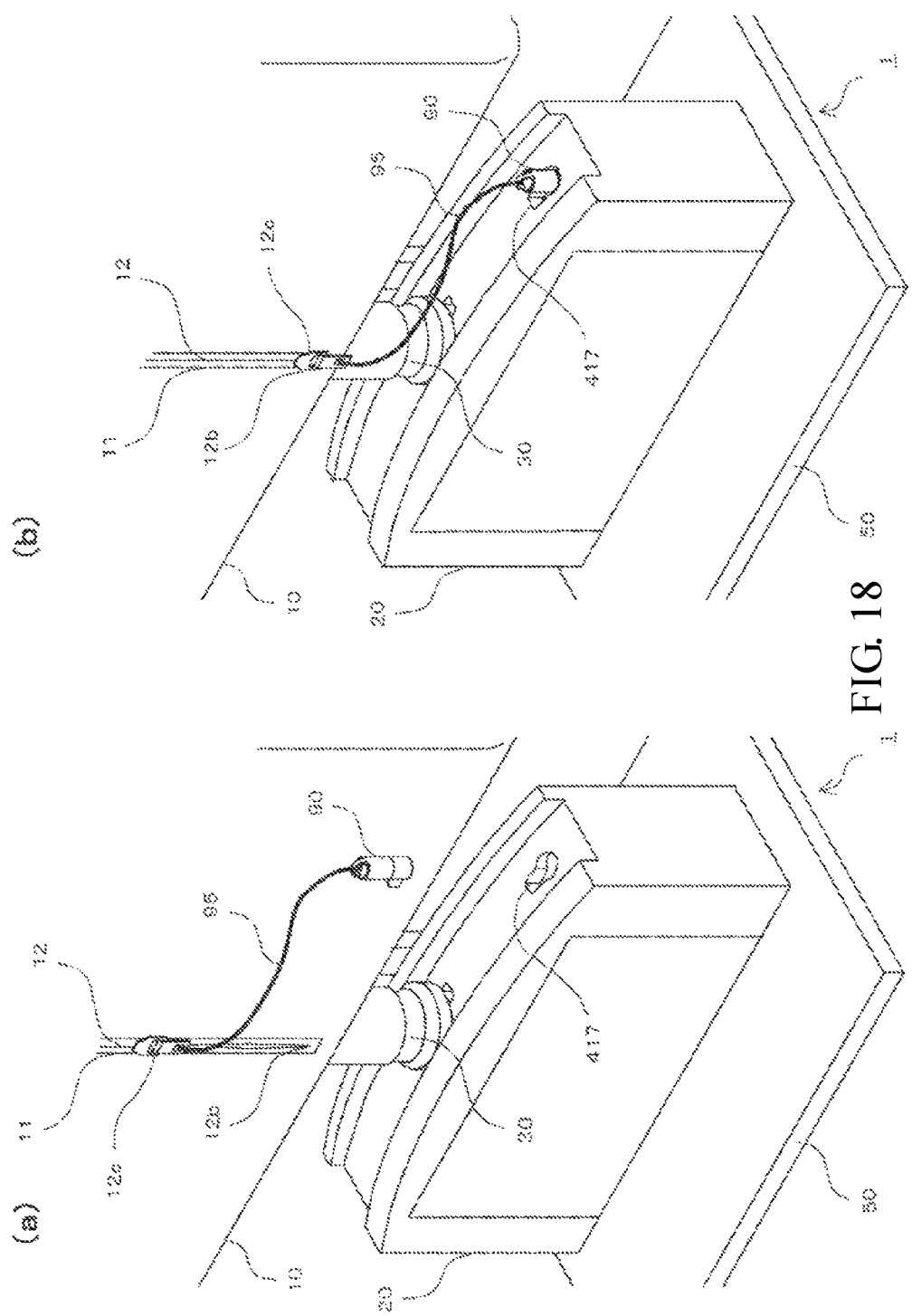
FIG. 18 is a diagram illustrating an action that a lock detection part detects that a throwing inlet of a bag body is locked by a zipper according to the embodiments.
Figure 19:
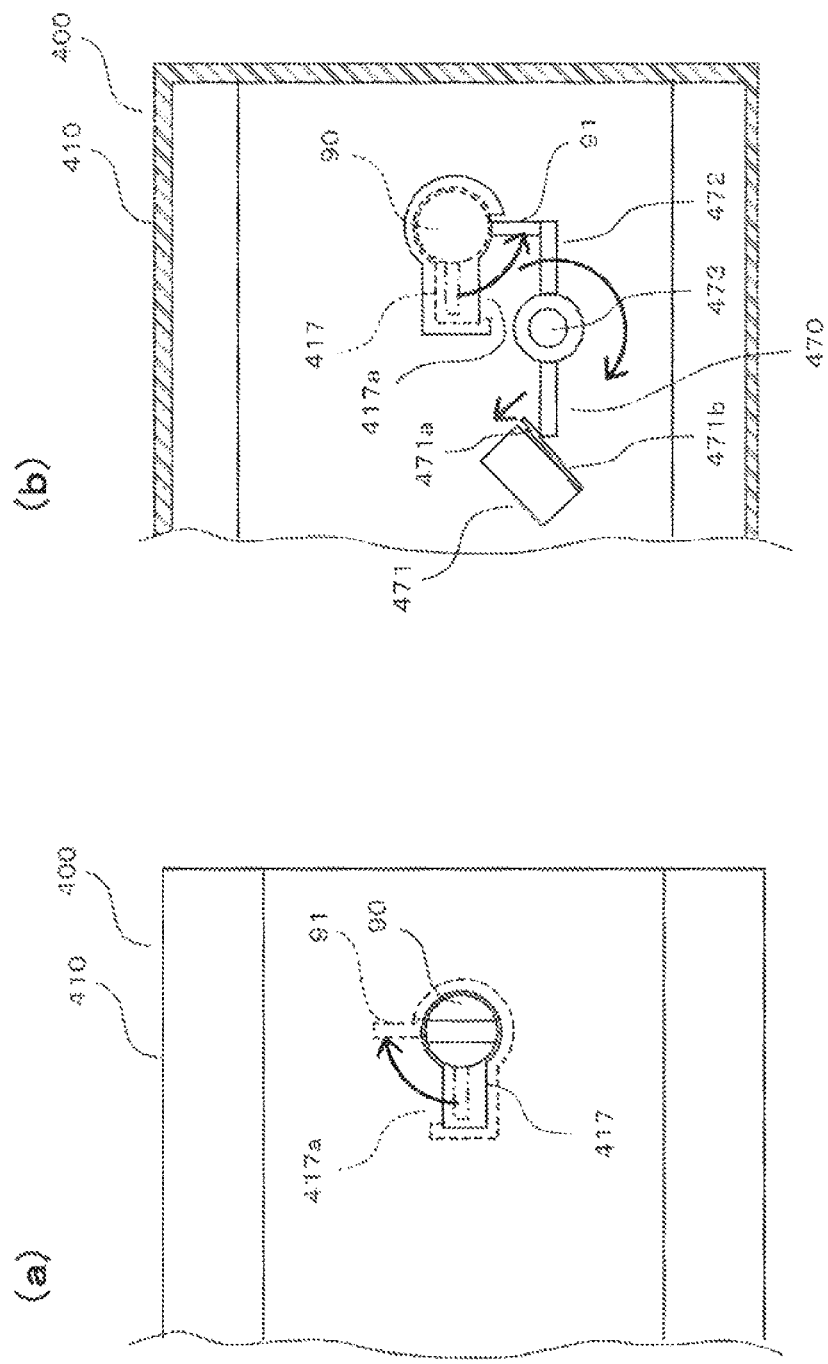
FIG. 19 is a diagram illustrating an action that the lock detection part detects that a throwing inlet of a bag body is locked by a zipper according to the embodiments.

Next, by referring to FIG. 18 to FIG. 19, an action that a lock detection part 470 detects that a throwing inlet 11 of a bag body 10 is locked by a zipper 12 is described.

A connecting rope 95 for connecting the detection lock 90 and the zipper slider 12*c* has a length that the detection lock 90 arrives at the lock inserting concave part 417 when the zipper 12 is locked to near the end part 12*b*. Therefore, as shown in FIG. 18(*a*), when the zipper slider 12*c* is not located near the end part 12*b*, the detection lock 90 fails to reach the lock inserting concave part 417 and the user cannot insert the detection lock 90 into the lock inserting concave part 417. Namely, at least in a state that the zipper 12 is completely unzipped, the detection lock 90 fails to reach the lock inserting concave part 417. On the other hand, as shown in FIG. 18(*b*), in a state that the zipper 12 is completely closed, the detection lock 90 can reach the lock inserting concave part 417 and be inserted into the lock inserting concave part 417.

When the user locks the throwing inlet 11 completely through the zipper 12, as shown in FIG. 19(*a*), the detection lock 90 is inserted into the lock inserting concave part 417 and the inserted detection lock 90 rotates to the right when being observed from the upper part. As shown in FIG. 19(*b*), the protruding part 91 of the detection lock 90 moves to the inner side of the upper surface of the housing body 410 through the opening part 417*a*, and one end of the relay rod 472 is pressed through the moved protrusion part 91. The relay rod 472 rotates; the rod part 471*b* is pressed through the other end of the relay rod 472; and the switch part 471*a* is pressed by the pressed rod part 471*b*. Thus, the detection switch 471 detects that the detection lock 90 has been inserted into the lock inserting concave part 417, i.e., detects that the throwing inlet 11 of the bag body 10 has been locked by the zipper 12.

It should be noted that when the detection lock 90 is removed from the lock inserting concave part 417, the rod part 471*b* rotates the relay rod 472 through elasticity itself, and simultaneously returns to an initial position. Thus, the detection switch 471 detects that the detection lock 90 has been removed from the lock inserting concave part 417.

Next, a detailed structure of the fragrance supply unit 80 is described.

Figure 20:
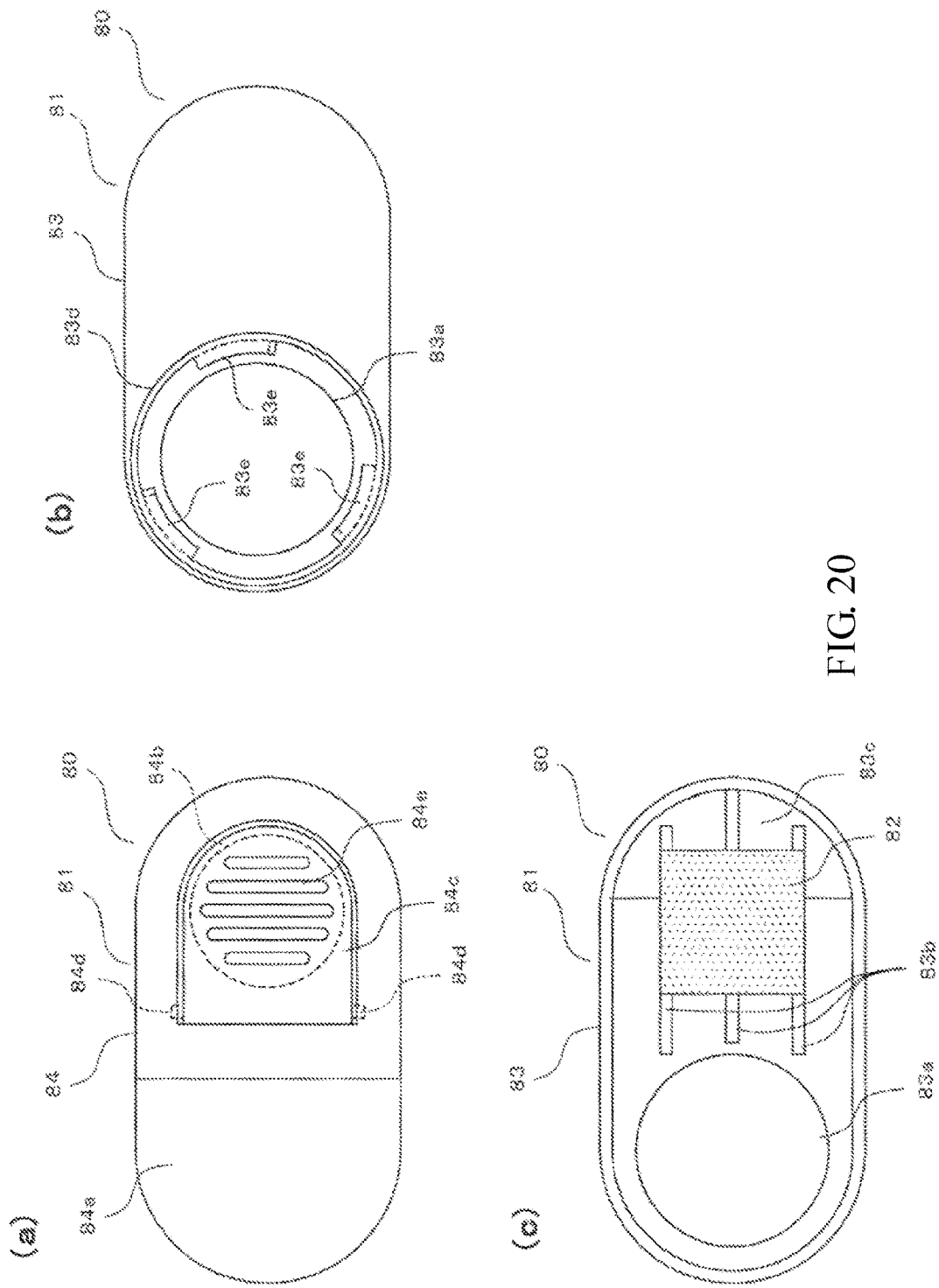
FIG. 20 is a structural diagram illustrating a fragrance supply unit according to the embodiments.
Figure 21:
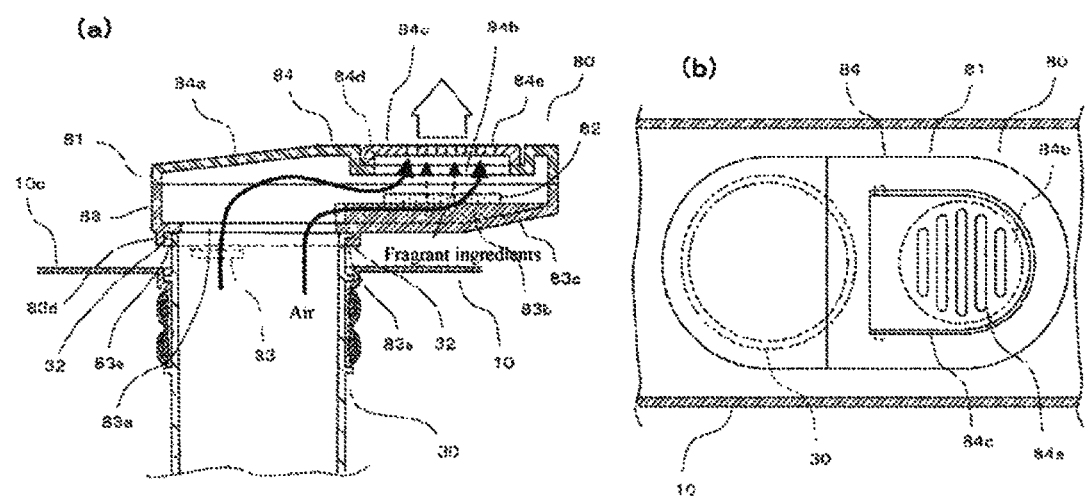
FIG. 21 is a structural diagram illustrating the fragrance supply unit according to the embodiments.

FIG. 20 and FIG. 21 are structural diagrams illustrating a fragrance supply unit 80. FIGS. 20(*a*) and 20(*b*) are a top view and a bottom view illustrating a fragrance supply unit 80 respectively. FIG. 20(*c*) is a top view illustrating a fragrance supply unit 80 in a state that an upper box body 84 is removed. FIG. 21 is a longitudinal section view illustrating a central part of a lower part of a bag body 10 in a state that a fragrance supply unit 80 is arranged on an introduction pipe 30. FIG. 21(*b*) is a cross section view illustrating a central part of a lower part of a bag body 10 in a state that a fragrance supply unit 80 is arranged on an introduction pipe 30.

The fragrance supply unit 80 includes an accommodating box 81 which has an oval box shape when observed from the top, and a fragrant body 82 accommodated in the accommodating box 81. The accommodating box 81 includes a lower box body 83 with an opened upper surface and an upper box body 84 with an opened bottom surface.

At the bottom surface of the lower box body 83, an air suction port 83*a* is formed at one end of a long edge direction, and a plurality of ribs 83*b* adjacent to the air suction port 83*a* and extending along the long edge direction are formed. The fragrant body 82 is loaded above the plurality of ribs 83*b*. In addition, on the other end, the bottom surface of the lower box body 83 has an inclined surface 83*c* which becomes higher to the other end. Moreover, at the bottom surface of the lower box body 83, a cylindrical connecting port 83*d* is formed in the manner of encircling the air suction port 83*a*. Claw parts 83*e* are formed in positions that the connecting port 83*d* corresponds to the clamping pieces 32 of the introduction pipe 30.

The upper box body 84 is arranged on the upper surface of the lower box body 83. The upper surface of the upper box body 84 has an inclined surface 84*a* which becomes higher to the other end in a position opposite to the air suction port 83*a*. In addition, an opening part 84*b* is formed in a position opposite to a plurality of ribs 83*b* on the upper surface of the upper box body 84. The opening part 84*b* is covered by a cover part 84*c* in an openable and closable manner. The cover part 84*c* rotates by taking a hinging part 84*d* as a center. A plurality of slit-shaped vent holes 84*e* are formed in the cover part 84*c*.

The fragrant body 82 is formed by porous material and the like which can be immersed in a liquid flavoring agent. The user opens the cover part 84*c* and puts the fragrant body 82 into the accommodating box 81 from the opening part 84*b*.

When the fragrance supply unit 80 is arranged in the introduction pipe 30, the connecting port 83*d* is inserted into the top part of the introduction pipe 30 in a state that the claw parts 83*e* and the clamping pieces 32 are staggered in positions. Then, the fragrance supply unit 80 rotates to overlapping positions of the claw parts 83*e* and the clamping pieces 32. As shown in FIG. 21(*a*), the clamping pieces 32 and the claw parts 83*e* are clamped and the fragrance supply unit 80 does not fall off upwards. It should be noted that the side fabric 10*c* of the lower surface of the bag body 10 can be prevented from being engaged between the connecting port 83*d* and the introduction pipe 30 since the front flange part 33 and the rear flange part 34.

As shown in FIG. 21(*b*), in a state that the fragrance supply unit 80 is arranged on the introduction pipe 30, the fragrance supply unit 80 is arranged in the bag body 10 in such a manner that a long edge direction of the fragrance supply unit 80 forms a left-right direction of the bag body 10. As mentioned above, since the introduction pipe 30 is fixed to the cylindrical part 15 in the manner of not rotating relative to the bag body 10, the fragrance supply unit 80 correctly arranged on the introduction pipe 30 does not come into contact with the front surface and the rear surface of the bag body 10.

Next, the deodorization operation and the fragrance increasing operation performed on the clothing deodorizing apparatus 1 are described.

Under the condition of performing the deodorization operation, the user accommodates the clothing hanged on the clothing rack H into the bag body 10 hanged on the bag body retention part 70. At this moment, as shown in FIG. 10(*b*), the user hangs the clothing in the bag body 10 to the second retention part 121 of the clothing rack retention part 42 by using the clothing rack H. In this way, in the bag body 10, the clothing is hanged through the clothing rack retention part 42. The user presses the deodorization button 452 of the operation part 450. When the pipe detection switch 460 detects that the introduction pipe 30 has been mounted on the ozone supply apparatus 20, and the lock detection part 470 detects that the lock 90 has been inserted into the lock inserting concave part 417, i.e., when a condition that the throwing inlet 11 of the bag body 10 is locked by the zipper 12 is detected, the control unit 900 starts the deodorization operation to enable the blowing fan 700 and the ozone generator 600 to operate. When the introduction pipe 30 has not been mounted on the ozone supply apparatus 20, the control unit 900 does not start the deodorization operation and enables the first informing part 454 to illuminate a lamp. In addition, when the throwing inlet 11 is not locked, the control unit 900 does not start the deodorization operation and enables the second informing part 455 to illuminate a lamp.

When the deodorization operation is started, outside air is taken into the air suction pipe 810 through the air suction port 418, and the dust and ozone included in the air can be removed through the dust filter 820 and the ozone removing filter 830 in the air suction pipe 810. The air without dust and ozone is delivered into the vent pipe 500 through the blowing fan 700 (with reference to an arrow in FIG. 16(*b*)). The air flowing in the vent pipe 500 is mixed with the ozone generated by the ozone generator 600 when passing through the ozone generator 600. In this way, the air with the ozone arrives at the exhaust port 414 through the vent pipe 500 and is exhausted from the exhaust port 414 (with reference to an arrow in FIG. 16(*a*)).

The air with the ozone exhausted from the ozone supply apparatus 20 is guided into the bag body 10 through the introduction pipe 30. As shown by an arrow in FIG. 1(*a*), the air with the ozone guided into the bag body 10 is in contact with the clothing in the bag body 10 from bottom to top and simultaneously flows. The clothing are deodorized through a deodorization effect of the ozone included in the air. Herein, although the lower part of the clothing is opened greatly, since the air with the ozone flows from bottom to top in the bag body 10, the air with the ozone is easy to spread over the inner part of the clothing. Thus, comprehensive deodorization can be performed on the outer side and the inner side of the clothing.

In addition, by hanging the bag body 10 to the bag body retention part 70, the clothing are hanged on the clothing rack H, thereby ensuring a clearance between the upper part of the bag body 10 and a shoulder part of the clothing. Thus, since the ozone is also easy to spread over the shoulder part of the clothing, the deodorization effect can be enhanced.

The air with a reduced ozone concentration because of the deodorization for the clothing, as shown by a dotted arrow in FIG. 1(*a*), is exhausted outside of the bag body 10 through the exhaust part 41 above the bag body 10. The ozone is removed from deodorized air through the ozone removing filter 44 when the deodorized air passes through the exhaust part 41. Thus, the concentration of the ozone in the air exhausted from the bag body 10 is further reduced.

Next, under the condition of performing the fragrance increasing operation, the user accommodates the clothing into the bag body 10 hanged on the bag body retention part 70, and as shown in FIG. 21, in the bag body 10, the fragrance supply unit 80 provided with the fragrant body 82 is arranged on the introduction pipe 30. The user presses the fragrance increasing button 453 of the operation part 450. When the pipe detection switch 460 detects that the introduction pipe 30 has been arranged on the ozone supply apparatus 20, and when the lock detection part 470 detects that the throwing inlet 11 of the bag body 10 has been locked by the zipper 12, the control unit 900 starts the fragrance increasing operation and enables the blowing fan 700 to operate. When the introduction pipe 30 is not arranged on the ozone supply apparatus 20, the control unit 900 does not start the fragrance increasing operation and enables the first informing part 454 to illuminate a lamp. In addition, when the throwing inlet 11 is not locked, the control unit 900 does not start the fragrance increasing operation and enables the second informing part 455 to illuminate a lamp.

When the fragrance increasing operation is started, as shown in FIG. 21(*a*), the air exhausted from the introduction pipe 30 is introduced into the accommodating box 81 from the air suction port 83*a*. The introduced air flows upwards after flowing towards the other end along a plurality of ribs 83*b*. Through the air that passes through the fragrant body 82, the fragrant ingredients included in the fragrant body 82 volatilize, and are mixed into the air. The air with the fragrant ingredients is exhausted into the bag body 10 through the opening part 84*b* and the vent hole 84*e*. It should be noted that the air successfully flows in the accommodating box 81 through two inclined surfaces 83c and 84a arranged on the accommodating box 81.

Similar to the condition of the deodorization operation, the air with the fragrant ingredients flows from bottom to top in the bag body 10. In addition, since air pressure in the bag body 10 is increased, a fragrance increasing effect of the clothing can be enhanced.

Effects of Present Embodiment

The following effect can be realized through the present embodiment.

(1) Since the clothing deodorizing apparatus 1 adopts such a structure that the air with the ozone supplied by the ozone supply apparatus 20 and the air with the fragrant ingredients is supplied to the bag body 10 for accommodating the clothing to perform the deodorization and fragrance increasing operation of the clothing, clothing deodorizing apparatus 1 can be easily arranged in a family without a large arrangement space.

(2) The introduction pipe 30 is fixed in the manner of not separating from the bag body 10 and also not rotating relative to the bag body 10. Thus, the orientation of the bag body 10 and the orientation of the ozone supply apparatus 20 can keep the desired relationship. Namely, the relationship that the front surface of the bag body 10 and the front surface of the ozone supply apparatus 20 face the same direction can be kept.

(3) Since the prevention unit for preventing the introduction pipe 30 from rotating relative to the bag body 10 is composed of the bundling belt 19 wound on the cylindrical part 15 to fasten the cylindrical part 15 inwards, and the protruding strip part 37 formed on the introduction pipe 30 in the manner of being clamped with the connecting part 19c of the bundling belt 19, the bundling belt 19 can be used to effectively prevent the introduction pipe 30 from rotating relative to the bag body 10.

(4) In the cylindrical part 15, the belt part 19b of the bundling belt 19 passes through the belt penetrating part 16, and the connecting part 19c which is exposed instead of passing through the belt penetrating part 16 is shielded by the shielding part 17. Therefore, the bundling belt 19 is difficult to be seen from outside, so that the appearance of the cylindrical part 15 is beautiful.

(5) The upper part and the lower part of the bag body 10 are retained respectively on the bag body retention part 70 and the ozone supply apparatus 20 in such a manner that the front surface of the bag body 10 and the front surface of the ozone supply apparatus 20 face the same direction. In this case, since the introduction pipe 30 can be prevented from rotating relative to the bag body 10, a condition of torsion of the bag body 10 due to change of the orientation of the lower part of the bag body 10 caused by rotation of the introduction pipe 30 is difficult to occur. By preventing the torsion of the bag body 10 in this way, the air with ozone can be successfully circulated in the bag body 10.

Variation Embodiment

Although the embodiments regarding the present disclosure are described above, the present disclosure is not limited to the above-mentioned embodiments. In addition, various changes except for the above can also be made to embodiments of the present disclosure.

Figure 22:
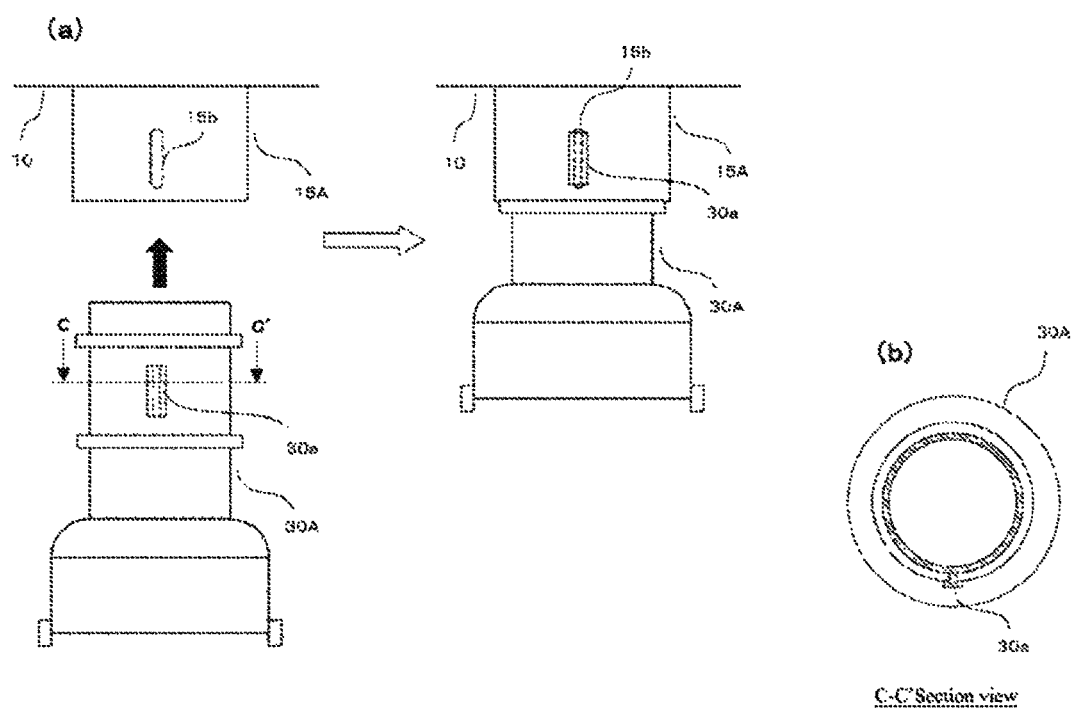
FIG. 22 is a structural diagram illustrating a clothing deodorizing apparatus according to the variation embodiments.

In the above embodiments, the prevention unit is provided, which prevent the introduction pipe 30 from rotating relative to the bag body 10 through the connecting part 19c of the bundling belt 19 and the protruding strip part 37 clamped with the connecting part 19c. However, the prevention unit can also adopt other structures as long as the structures can prevent the introduction pipe 30 from rotating relative to the bag body 10. For example, structures shown in FIGS. 22(a) and (b) can be adopted. Namely, the protruding strip part 30a having a T-shaped section and extending upwards and downwards is formed on the introduction pipe 30A. On the other hand, a slit hole 15b which is long in an up-down direction is formed in the cylindrical part 15A of the bag body 10. When the introduction pipe 30A is arranged on the cylindrical part 15A, the protruding strip part 30a passes through the slit hole 15b. Then, the bundling belt (not shown) is wound in a proper position of the cylindrical part 15A, and the introduction pipe 30A is fixed to the cylindrical part 15A through the fastening of the bundling belt. The introduction pipe 30 is clamped with the protruding strip part 30a through the slit hole 15b and does not rotate relative to the bag body 10.

Then, in the above embodiments, the introduction pipe 30 is fixed to the cylindrical part 15 through two bundling belts 19, i.e., an upper bundling belt and a lower bundling belt. However, the number of the bundling belts 19 is not limited to two, and can also be one or more than three.

In addition, various changes can be properly made to the embodiments of the present disclosure within a scope of technical concepts shown in a scope of claims.

LIST OF REFERENCE NUMERALS

10: bag body; 15: cylindrical part (fixing part); 16: belt penetrating part; 17: shielding part; 19: bundling belt; 20: ozone supply apparatus; 30: introduction pipe; 37: protruding strip part (protruding part); 50: base; 60: supporting post; 70: bag body retention part; 413: inserting port part (installation part).

The invention claimed is:

1. A clothing treatment apparatus, comprising:
   a bag body for accommodating clothes;
   an ozone supply apparatus for supplying air with ozone into the bag body;
   an introduction pipe for guiding the air with the ozone exhausted from the ozone supply apparatus into the bag body;
   a fixing part formed on the bag body and fixed with one end part of the introduction pipe, the one end part of the introduction pipe is cylindrical, and the fixing part is cylindrical and encircles the one end part of the introduction pipe;
   an installation part formed on the ozone supply apparatus and configured to detachably install the other end part of the introduction pipe in a specified orientation, wherein
   a prevention unit for preventing the introduction pipe from rotating is arranged between the one end part of the introduction pipe and the fixing part along an in-plane direction perpendicular to an installation direction of the introduction pipe to the fixing part; and
   the prevention unit comprises:
   a bundling belt wound on the fixing part that encircles the one end part of the introduction pipe and configured to fasten the fixing part inwards; and
   a protruding part formed on the one end part of the introduction pipe and clamped on a connecting part between a head and a belt part of the bundling belt.

2. The clothing treatment apparatus according to claim 1, wherein
the fixing part comprises:
a belt penetrating part for the belt part to penetrate through; and
a shielding part for shielding the connecting part which is exposed to the fixing part instead of penetrating through the belt penetrating part.

3. The clothing treatment apparatus according to claim 1, wherein the clothing treatment apparatus further comprises:
a base for fixing the ozone supply apparatus;
a supporting post extending upwards from the base; and
a bag body retention part arranged on an upper end of the supporting post so as to retain an upper part of the bag body in such a manner that a front surface of the bag body and one surface of the ozone supply apparatus face the same direction, wherein
the introduction pipe is arranged on the ozone supply apparatus in such a manner that the front surface of the bag body and the one surface of the ozone supply apparatus face the same direction.

\* \* \* \* \*